(12) United States Patent
Seitz et al.

(10) Patent No.: US 12,186,457 B2
(45) Date of Patent: Jan. 7, 2025

(54) SPHINGOLIPID COATINGS AND PROCESS FOR MANUFACTURING SPHINGOLIPID COATINGS EFFECTIVE FOR INHIBITING BIOFILM FORMATION

(71) Applicant: UNIVERSITY OF CINCINNATI, Cincinnati, OH (US)

(72) Inventors: Aaron Seitz, Cincinnati, OH (US); Michael J. Edwards, Cincinnati, OH (US); Erich Gulbins, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 16/060,455

(22) PCT Filed: Dec. 9, 2016

(86) PCT No.: PCT/US2016/065838
§ 371 (c)(1),
(2) Date: Jun. 8, 2018

(87) PCT Pub. No.: WO2017/100580
PCT Pub. Date: Jun. 15, 2017

(65) Prior Publication Data
US 2018/0353656 A1    Dec. 13, 2018

Related U.S. Application Data

(60) Provisional application No. 62/265,659, filed on Dec. 10, 2015, provisional application No. 62/382,317, filed on Sep. 1, 2016.

(51) Int. Cl.
*A61L 29/16* (2006.01)
*A61M 16/04* (2006.01)
*A61M 25/00* (2006.01)

(52) U.S. Cl.
CPC ............ *A61L 29/16* (2013.01); *A61M 16/04* (2013.01); *A61L 2300/22* (2013.01); *A61L 2300/404* (2013.01); *A61M 25/0009* (2013.01); *A61M 25/0017* (2013.01); *A61M 25/0045* (2013.01); *A61M 2205/0205* (2013.01); *A61M 2205/0238* (2013.01); *A61M 2207/00* (2013.01)

(58) Field of Classification Search
None
See application file for complete search history.

(56) References Cited

U.S. PATENT DOCUMENTS

| | | | |
|---|---|---|---|
| 4,489,722 A | 12/1984 | Ferraro et al. | |
| 5,562,922 A * | 10/1996 | Lambert | A61L 27/34 424/427 |
| 6,682,545 B1 * | 1/2004 | Kester | A61K 31/133 604/103.01 |
| 2001/0018072 A1 | 8/2001 | Unger | |
| 2003/0124228 A1 | 7/2003 | Goto et al. | |
| 2004/0201117 A1 | 10/2004 | Anderson | |
| 2007/0080323 A1 | 4/2007 | Joabsson et al. | |
| 2008/0118544 A1 * | 5/2008 | Wang | A61K 31/337 424/423 |
| 2009/0099651 A1 | 4/2009 | Hakimi-Mehr et al. | |
| 2010/0021531 A1 | 1/2010 | Yoshino et al. | |
| 2013/0052237 A1 | 2/2013 | Eliaz et al. | |
| 2015/0147361 A1 | 5/2015 | Bikker et al. | |

FOREIGN PATENT DOCUMENTS

| | | | | |
|---|---|---|---|---|
| EP | 0245799 B1 | 10/1991 | | |
| WO | WO-2011061237 A1 * | 5/2011 | ............ | A61K 31/19 |

OTHER PUBLICATIONS

Markham, Jonathan E. "Detection and quantification of plant sphingolipids by LC-MS." Plant Lipid Signaling Protocols. Humana Press, Totowa, NJ, 2013. 93-101. (Year: 2013).*
Cuvillier O. Sphingosine in apoptosis signaling. Biochimica Et Biophysica Acta (BBA)—Molecular and Cell Biology of Lipids. Dec. 30, 2002;1585(2-3):153-62. (Year: 2002).*
Chandrapala J, Martin GJ, Kentish SE, Ashokkumar M. Dissolution and reconstitution of casein micelle containing dairy powders by high shear using ultrasonic and physical methods. Ultrasonics sonochemistry. Sep. 1, 2014;21(5):1658-65. (Year: 2014).*
Definition of "stable" from dictionary.com, accessed May 4, 2022 (Year: 2022).*
Definition of "durable" from dictionary.com, accessed May 4, 2022 (Year: 2022).*
Definition of "detect" from thefreedictionary.com, accessed May 30, 2023 (Year: 2023).*
International Search Report & Written Opinion for corresponding PCT Application No. PCT/US2016/065838 mailed Feb. 27, 2017.

* cited by examiner

*Primary Examiner* — Nissa M Westerberg
(74) *Attorney, Agent, or Firm* — Dinsmore & Shohl LLP

(57) ABSTRACT

Methods for applying a sphingolipid aggregate coating to a surface of a substrate for inhibition and prevention of biofilm growth, methods for inhibiting and preventing biofilms, biofilm-inhibiting coatings and coated devices are provided. Coating processes include suspending an amount of sphingolipid in a medium-to-fast-evaporating organic solvent; b) applying energy to the suspension sufficient to create a colloidal dispersion of sphingolipid in the solvent; c) heating the dispersion sufficient to create a solution; and d) coating the surface of the substrate with at least one application of solution, each application followed directly by a complete solvent evaporation period. The resulting coatings exhibit aggregate architectures particularly effective for inhibition and prevention of biofilms.

19 Claims, 31 Drawing Sheets

IN VITRO:A. BAUMANNII
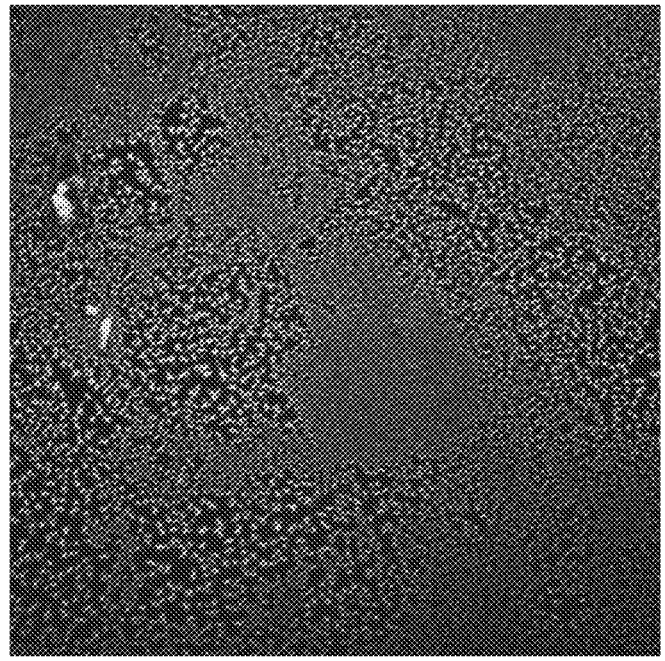
HEXANE COATED
IN VITRO:A. BAUMANNII
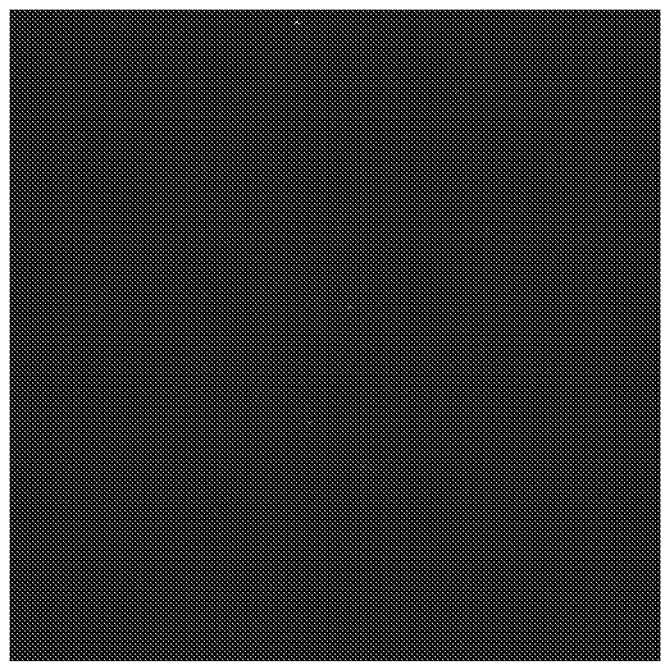
SPHINGOSINE:HEXANE COATED
FIG. 2A IN VITRO P. AERUGINOSA
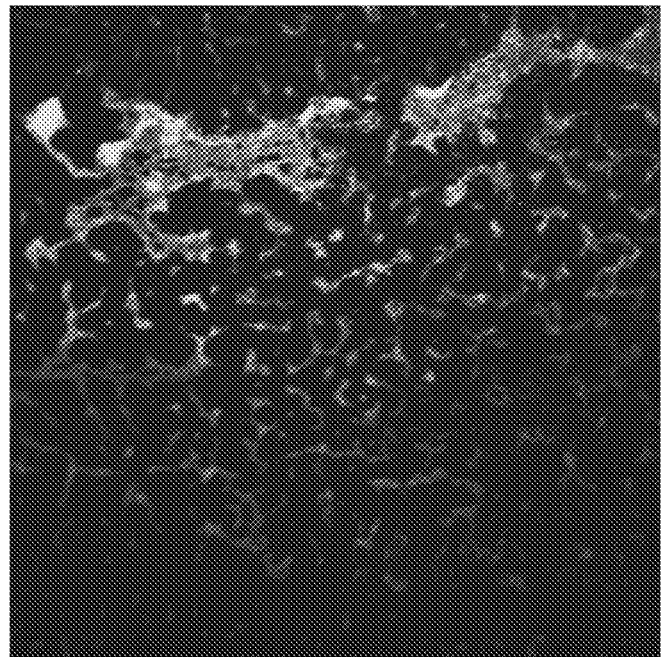
HEXANE COATED
IN VITRO P. AERUGINOSA
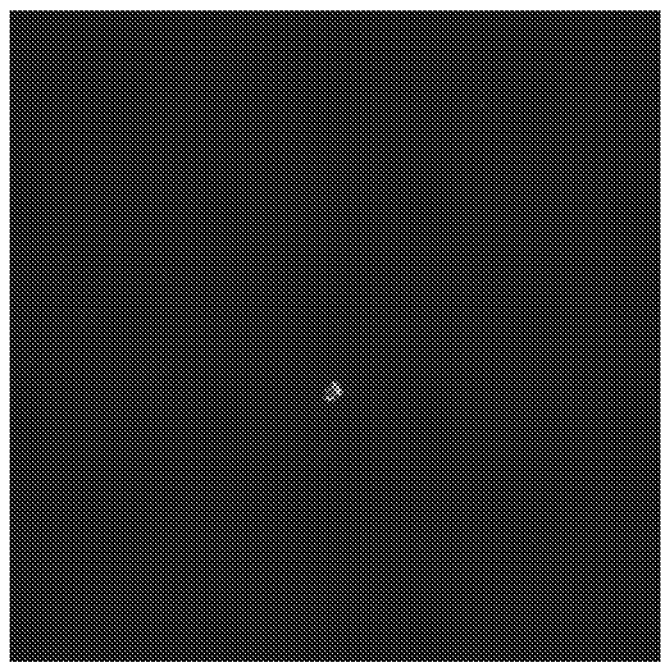
SPHINGOSINE:HEXANE COATED
FIG. 2B IN VITRO A BAUMANNII
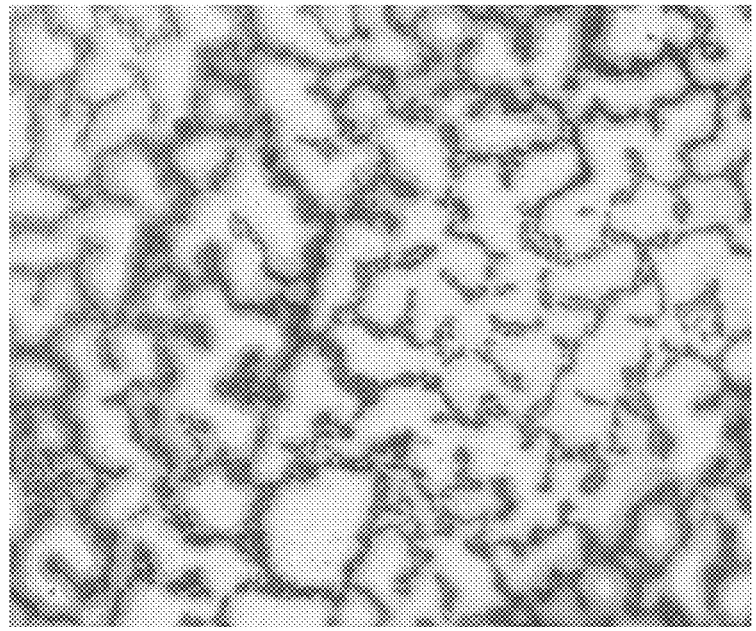
ACETONE COATED
IN VITRO A BAUMANNII
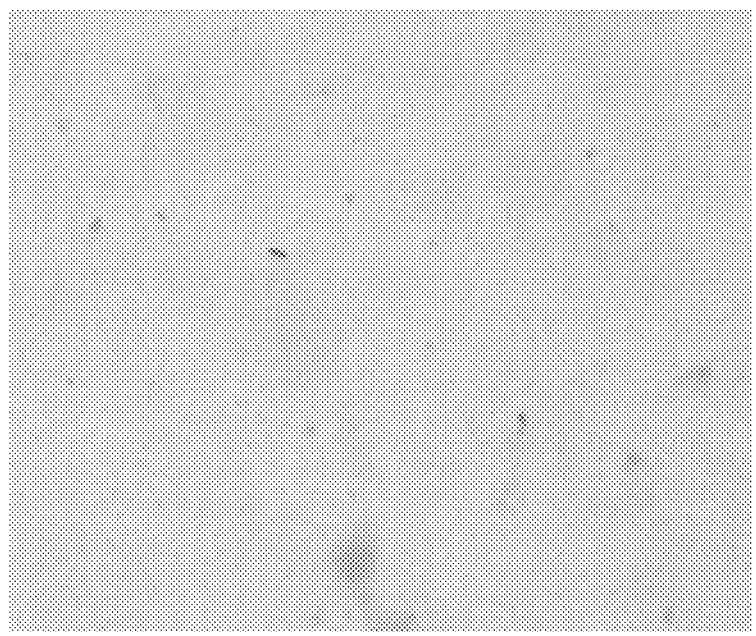
PHYTOSPHIN PhytoSPH IN VITRO – 2015.08.03

| GROUP | BACT | PLATE 1 (CFU) | PLATE 2 (CFU) | PLATE 3 (CFU) | PLATE 4 (CFU) | PLATE 5 (CFU) | AVERAGE (CFU) | STD DEV | STD ERROR | T-TEST VS CONTROL | % REDUCTION | LOG REDUCTION |
|---|---|---|---|---|---|---|---|---|---|---|---|---|
| 30mM.PhytoSPH.Acetone.Alum | AB | 8.80E+05 | 1.20E+07 | 6.00E+04 | | | 4.31E+03 | 5.45E+06 | 3.17E+03 | 0.004920764 | 98.15% | 1.73 |
| Acetone.Alum | AB | 2.40E+08 | 3.00E+08 | 1.60E+08 | | | 2.33E+08 | 5.73E+07 | 3.31E+07 | | | |
| 30mM.PhytoSPH.Acetone.Alum | PA | 1.50E+06 | 3.00E+06 | 2.00E+06 | | | 2.17E+06 | 6.24E+05 | 3.60E+05 | 0.011043113 | 93.98% | 1.22 |
| Acetone.Alum | PA | 5.10E+07 | 2.70E+07 | 3.00E+07 | | | 3.60E+07 | 1.07E+07 | 6.16E+06 | | | |
| 30mM.PhytoSPH.Acetone.Alum | SA | 2.30E+05 | 2.00E+05 | 2.00E+04 | | | 1.50E+05 | 9.27E+04 | 5.35E+04 | 0.048860416 | 99.69% | 2.51 |
| Acetone.Alum | SA | 1.80E+07 | 7.80E+07 | 5.00E+07 | | | 4.87E+07 | 2.45E+07 | 1.42E+07 | | | |
| 30mM.PhytoSPH.Acetone.PVC | AB | 1.60E+06 | 2.60E+06 | 2.60E+03 | 2.60E+03 | 6.60E+06 | 4.18E+06 | 2.39E+06 | 1.07E+06 | 0.000878302 | 99.01% | 2.00 |
| Acetone.PVC | AB | 6.70E+08 | 7.60E+08 | 2.00E+08 | 2.00E+08 | 2.80E+08 | 4.22E+08 | 2.43E+08 | 1.09E+08 | | | |
| 30mM.PhytoSPH.Acetone.PVC | PA | 3.50E+06 | 2.00E+06 | 2.20E+06 | 2.20E+06 | 2.90E+06 | 3.58E+06 | 5.49E+05 | 2.46E+05 | 1.0208E-06 | 89.68% | 0.99 |
| Acetone.PVC | PA | 2.30E+05 | 2.20E+07 | 2.80E+07 | 2.80E+07 | 3.00E+07 | 2.50E+07 | 3.35E+06 | 1.50E+06 | | | |
| 30mM.PhytoSPH.Acetone.PVC | SA | 6.10E+05 | 5.40E+05 | 7.00E+04 | 7.00E+04 | 1.30E+06 | 6.38E+05 | 3.93E+05 | 1.75E+05 | 3.24679E-06 | 99.38% | 2.21 |
| Acetone.PVC | SA | 1.10E+08 | 8.20E+07 | 1.10E+08 | 1.10E+08 | 8.40E+07 | 1.03E+08 | 1.80E+07 | 8.07E+06 | | | |

FIG. 5

PhytoSPH IN VITRO - 2015.10.20

| GROUP | BACT | N | AVERAGE(CFU) | STD DEV | STD ERROR | T-TEST VS CONTROL | % REDUCTION | LOG REDUCTION |
|---|---|---|---|---|---|---|---|---|
| EtOH_ADHERENT | AB | 10 | 1.15E+06 | 1.31E+06 | 4.15E+05 | 0.017218971 | 99.9999128% | 6.06 |
| 79mMPhytoSPHEtOH_ADHERENT | AB | 10 | 1.00E+00 | 0.00E+00 | 0.00E+00 | | | |
| EtOH_ADHERENT | PA | 10 | 9.80E+05 | 9.08E+02 | 3.87E+05 | 0.0049406 | 99.9468571% | 3.27 |
| 79mMPhytoSPHEtOH_ADHERENT | PA | 10 | 5.21E+02 | 1.53E+03 | 4.83E+02 | | | |
| EtOH_ADHERENT | MRSA | 10 | 2.47E+05 | 1.02E+05 | 3.23E+04 | 9.78909E-07 | 99.9793927% | 3.69 |
| 79mMPhytoSPHEtOH_ADHERENT | MRSA | 10 | 5.09E+01 | 1.50E+02 | 4.73E+01 | | | |

FIG. 7

SPHINGOLIPID THIN FILM IMAGING –
30 MM SPHINGOSINE –SYTO 9
CONTROL HEXANE
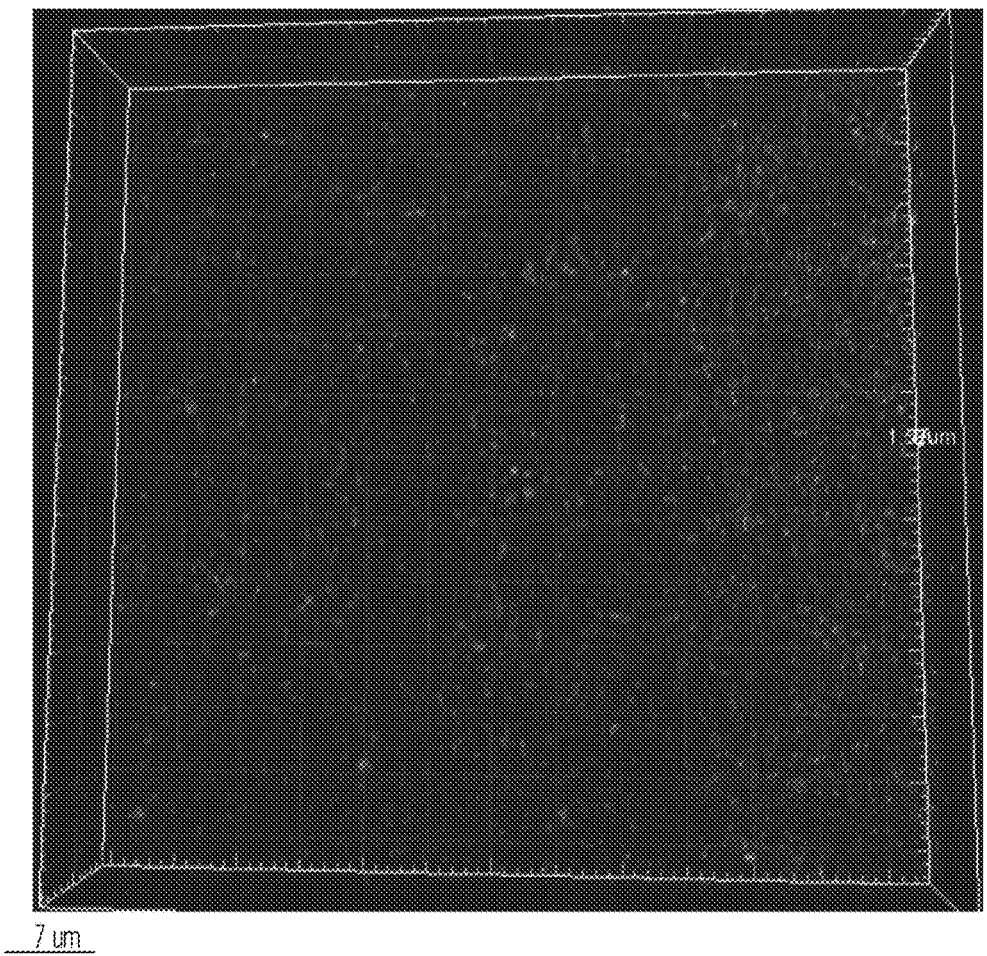
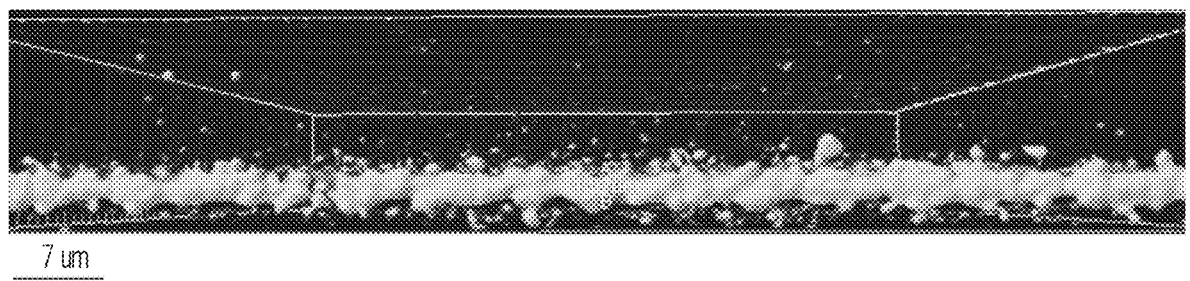
FIG. 9A

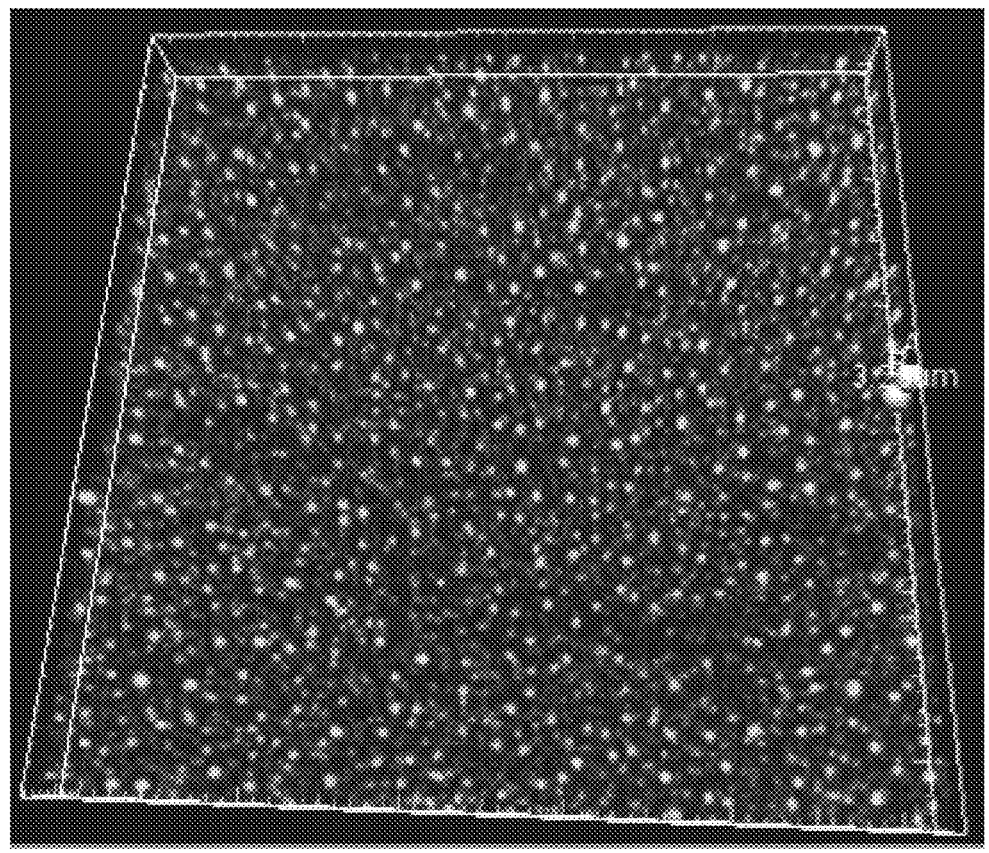
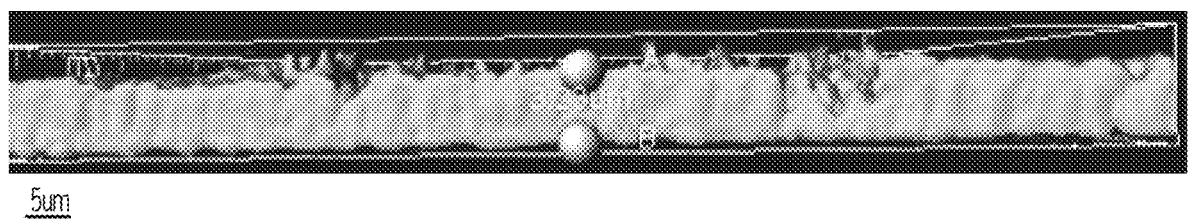
FIG 9B

SPHINGOLIPID THIN FILM IMAGING – 30 MM
SPHINGOSINE –SYTO 9
2DIPS
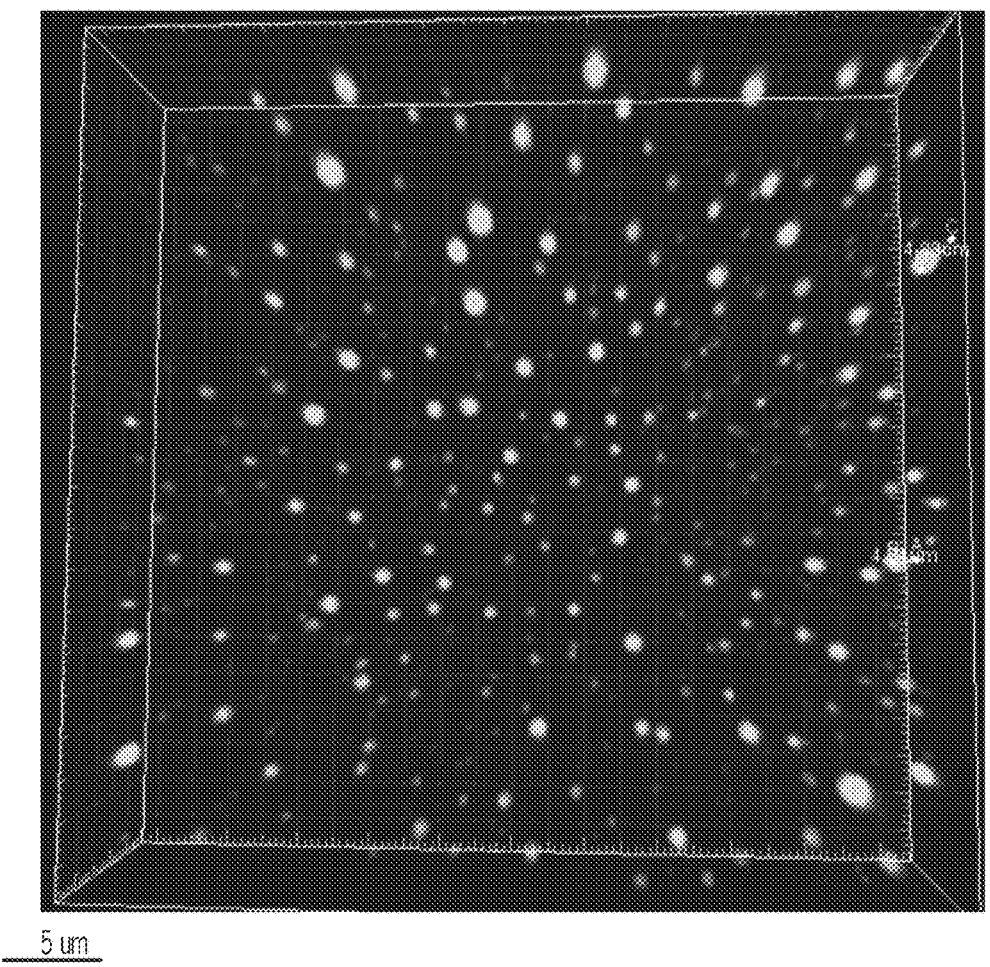
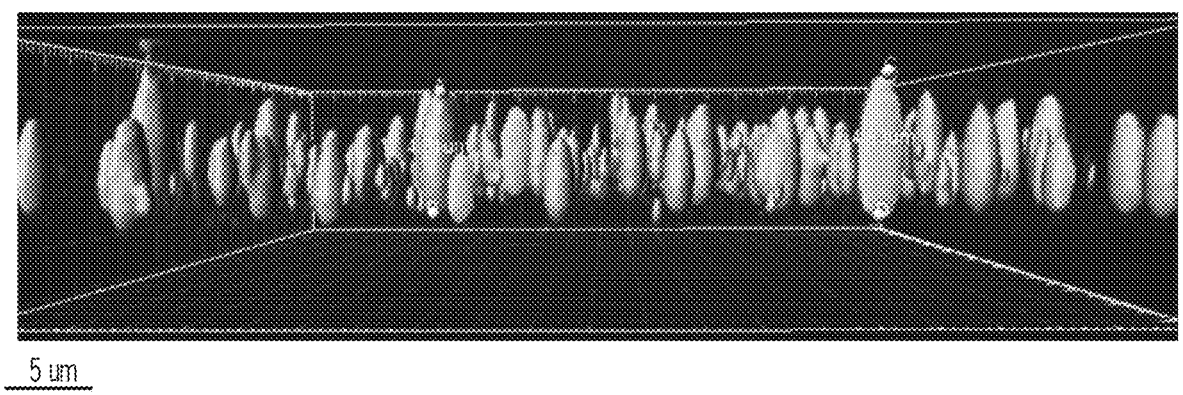
FIG. 9C SPHINGOLIPID THIN FILM IMAGING – 30 MM
SPHINGOSINE –SYTO 9
3 DIPS
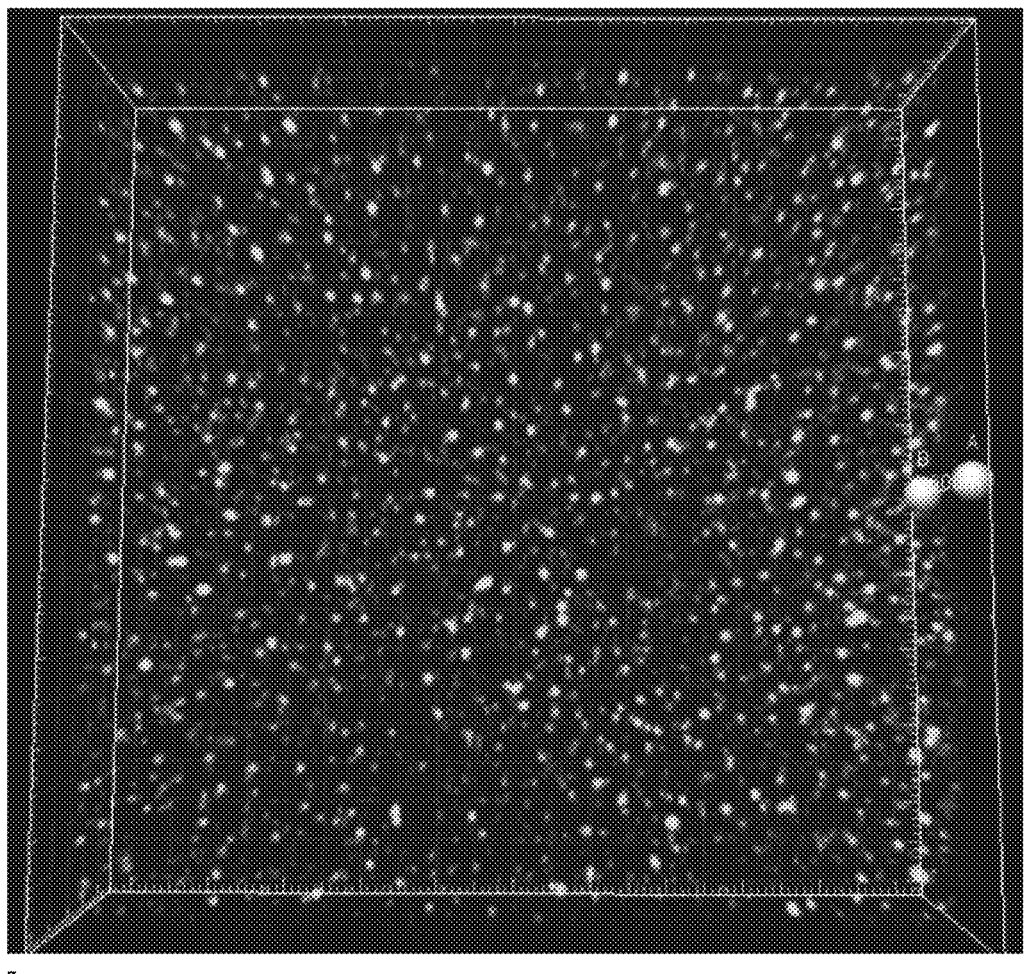
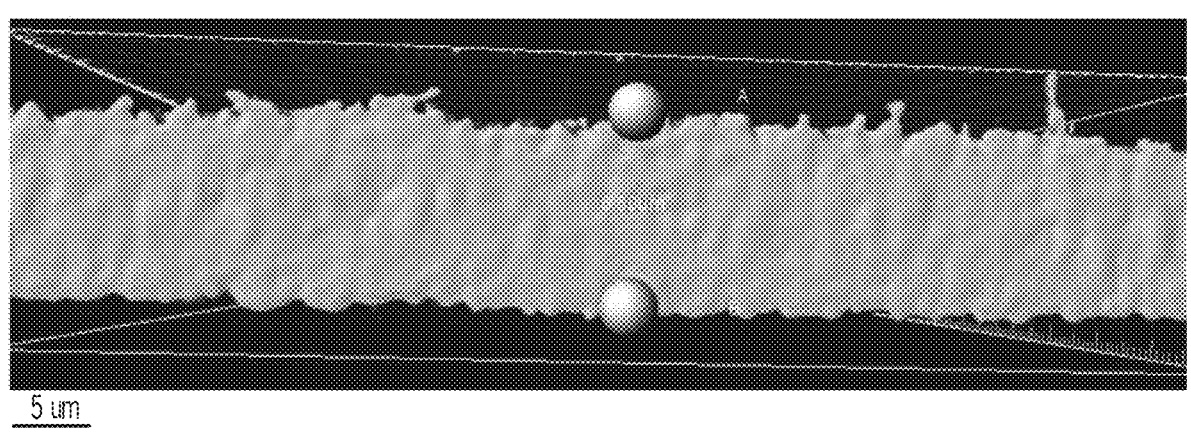
FIG. 9D SPHINGOLIPID THIN FILM IMAGING - 30 MM
SPHINGOSINE -SYTO 9
4 DIPS
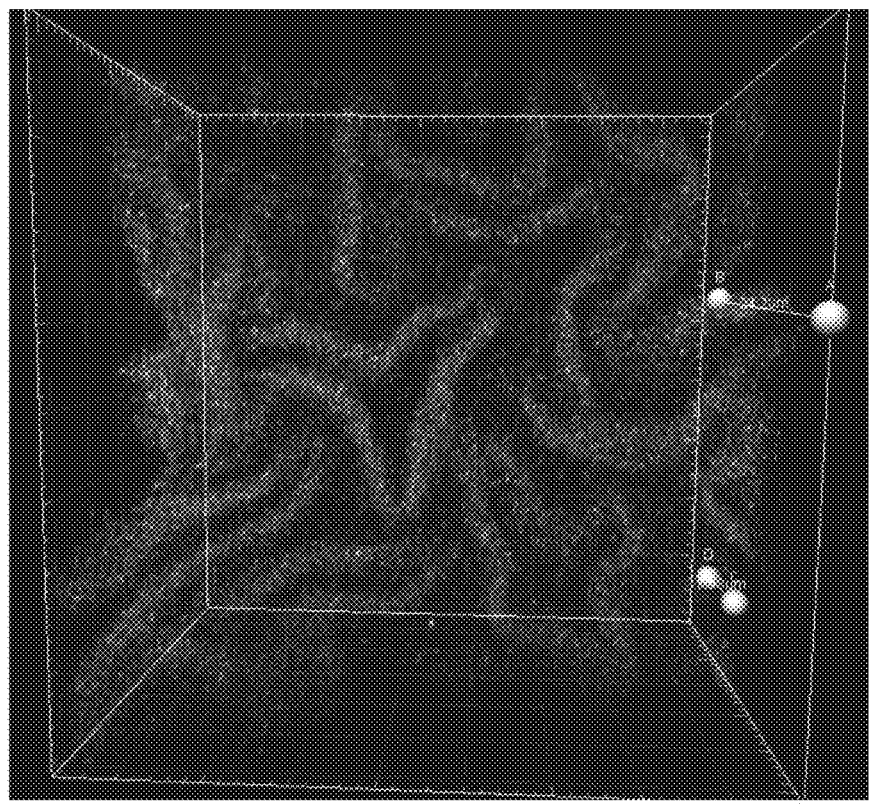
5 um
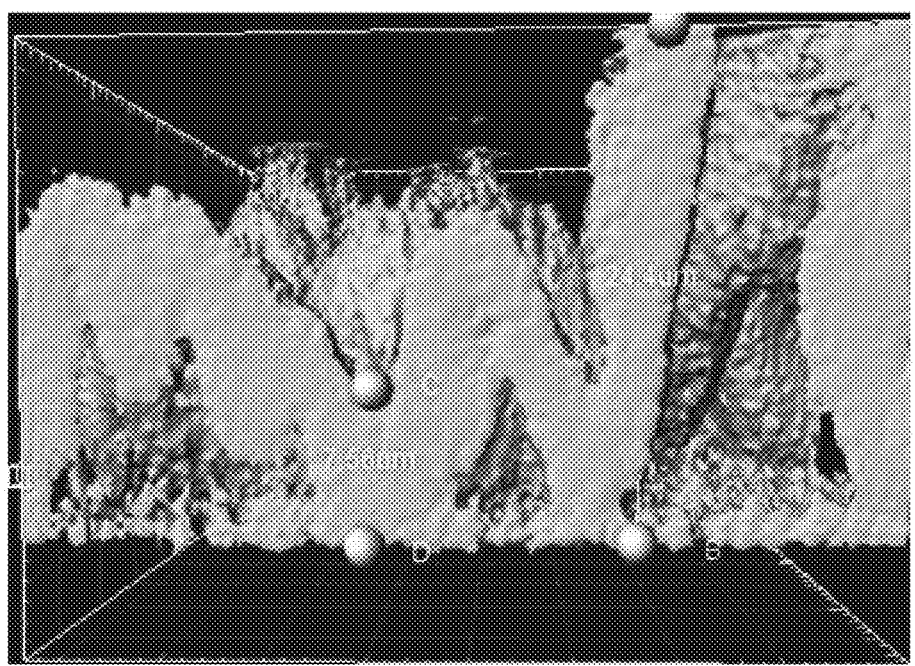
5 um
FIG. 9E

FIG. 12 (continued)
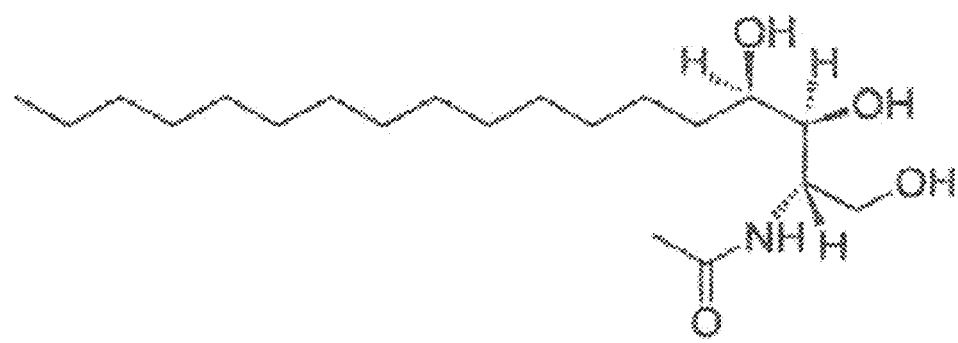
N-acetyl-phytosphingosine
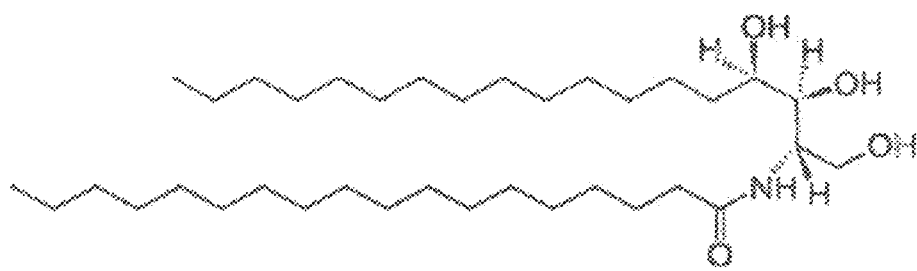
Stearoyl-phytosphingosine
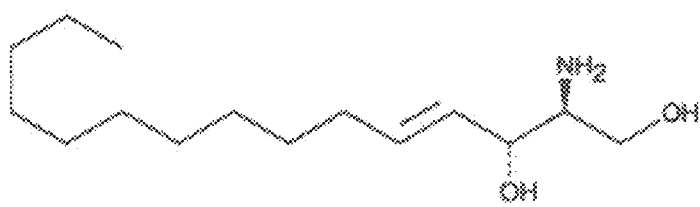
D-erythro-sphingosine C15

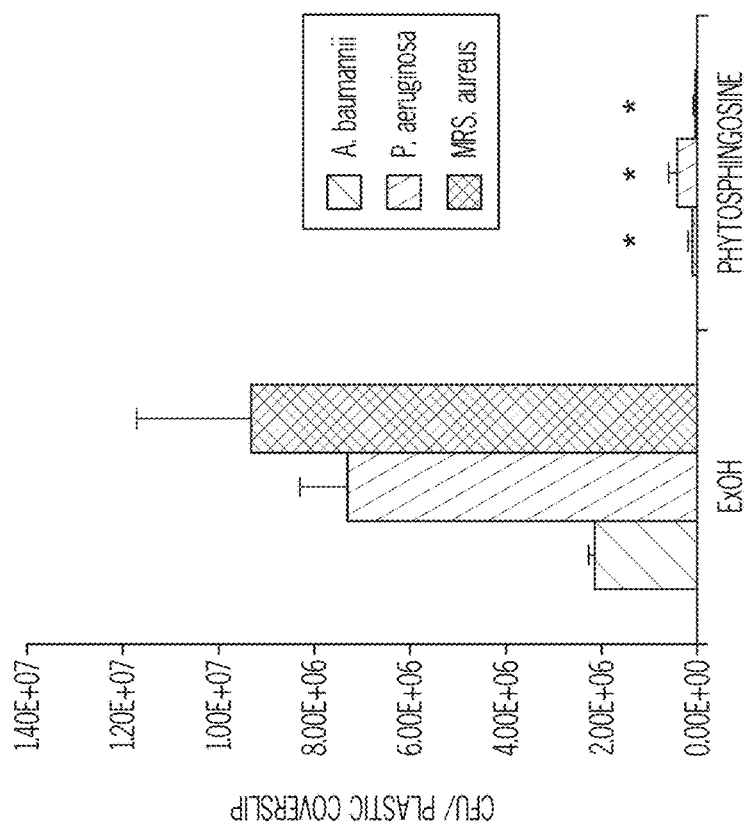
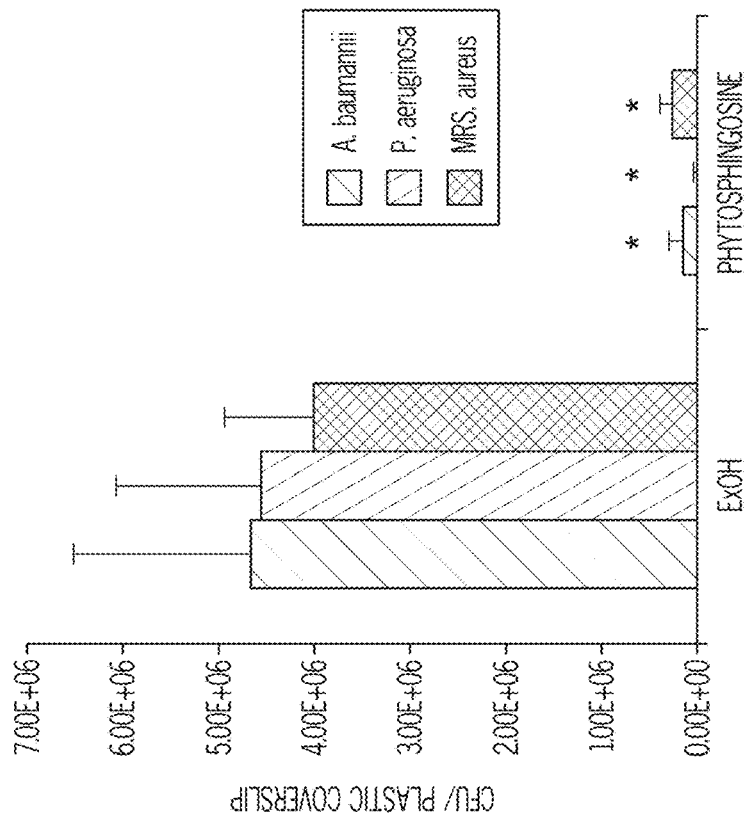
FIG. 14A
FIG. 14B

SPHINGOLIPID COATINGS AND PROCESS FOR MANUFACTURING SPHINGOLIPID COATINGS EFFECTIVE FOR INHIBITING BIOFILM FORMATION

PRIORITY CLAIM

This application is a § 371 U.S. National Stage application of International Application No. PCT/US2016/065838, filed Dec. 9, 2016, and claims priority to U.S. provisional application No. 62/265,659 filed Dec. 10, 2015, and U.S. provisional application No. 62/382,317 filed Sep. 1, 2016, the entire disclosures of which are incorporated herein.

STATEMENT REGARDING FEDERALLY SPONSORED RESEARCH OR DEVELOPMENT

This invention was made with government support under FA8650-14-2-6B33 awarded by the Air Force Research Laboratory. The government has certain rights in the invention.

TECHNICAL FIELD

Embodiments of the invention provide antimicrobial coatings particularly effective for inhibiting growth of biofilms on a variety of substrates, and processes for their manufacture.

BACKGROUND

In a 2009 CDC report, the cost of health care associated infections was estimated at approximately 28-45 billion dollars annually. Medical device related infections constitute a large portion of these infections. For example, it is reported that over 80,000 central venous catheter-related infections occur in ICUs annually. Hospital-acquired pneumonia (HAP) is the leading cause of death among hospital-acquired infections. Patients at highest risk of contracting HAP are those who are mechanically ventilated, and thus require the use of implanted endotracheal tubes (ETT). Ventilator associated pneumonia (VAP) occurs in 10-25% of mechanically ventilated patients and carries a mortality rate of between 9% and 13%.

It is widely accepted that medical device related infections are caused by biofilm formation on these devices. A biofilm is defined as a coherent cluster of bacterial cells imbedded in a biopolymer matrix, which, compared with planktonic cells, shows increased tolerance to antimicrobials and resists the antimicrobial properties of the host defense. Biofilms are found on up to 95% of endotracheal tubes (ETT) and such biofilms are substantially resistant to systemic administration of antibiotics. Biofilms are notoriously difficult to remove once established, and prevention of formation is a paramount technical goal.

One approach to inhibition of biofilm formation has been to coat surfaces of biomaterials/devices with antibiotics. For example, in one study, vancomycin was covalently bonded to the surface of a titanium alloy metal implant and formation of S. epidermidis biofilm was shown to be substantially inhibited. However, a serious drawback is that the use of antibiotics leads to development of antibiotic resistance and has been shown to actually induce biofilm formation.

Silver is known as one of the strongest bactericidal agents, and silver coatings demonstrated early promise against biofilm formation. However, coating medical devices with silver ions or metallic silver has had disappointing clinic results, probably due to inactivation of metallic silver when the devices contact blood and the coating wears. More recently biofilm formation by a number of pathogens such E. coli, Enterococcus, S. aureus, coagulase-negative Staphylococci on silver nanoparticle coated catheters was almost completely prevented in another experimental silver coating. Nonetheless, silver is problematic for use in implantable devices, or devices intended for prolonged contact with an internal cavity of a human subject, since silver nanoparticles are known to have genotoxic and cytotoxic effects on human cells at high doses. Further, accelerated thrombin formation and platelet activation were observed on surfaces of the catheters coated with the silver nanoparticles, which could increase the thrombosis risk generally.

Anti-adhesion coatings have also been studied for the effect of reducing attachment of pathogenic bacteria. The results, however, have been inconsistent. Further, anti-adhesion coatings may alter properties of the biomaterial, including chemical composition and reactivity, hydrophilicity and hydrophobicity, surface roughness and surface charge.

Many studies have shown that the surface roughness of biomaterials strongly influences the degree of bacterial attachment to surfaces. Thus, polishing was considered to have potential in reducing bacterial adherence and inhibition of biofilm formation. However, a recent study actually demonstrated greater attachment of S. aureus cells to mechanochemically polished titanium than to the original titanium device surface. The investigators speculated that mechanochemical polishing generated nanoscale surface features on the titanium surfaces with a characteristic pattern more suitable for anchoring of spherical S. aureus cells.

"Polymer brush" coatings were another type of promising anti-adhesion coating recently considered for inhibition of biofilms. Polymer brush coatings are formed when hydrophilic polymer long-chains are attached to a surface and stretch out into the surrounding medium. Excellent in vitro results demonstrated significant reduction in protein adsorption and bacterial adhesion, and predicted a high effectiveness in preventing bacterial adhesion. In contrast, in vivo results using polymer brush coatings have been discouraging mainly due to the weak surface attachment of polymer chains and the susceptibility of the polymer to oxidation damage that prevented successful applications of such coatings for in vivo conditions.

Sphingolipids, or glycosylceramides, are a class of lipids containing a backbone of sphingoid bases and a set of aliphatic amino alcohols. Sphingosine is the simplest in this family of biomolecular compounds. Representative species are set forth in FIG. 12 and below.

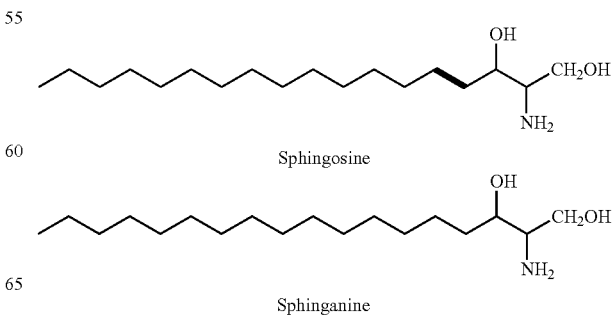

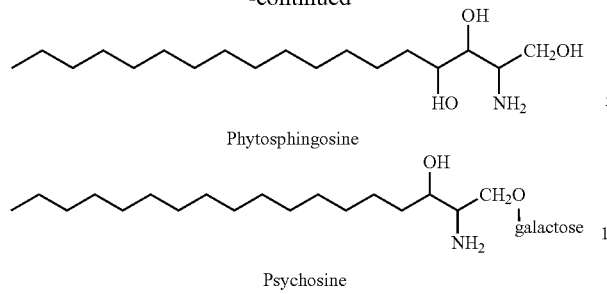

Phytosphingosine

Psychosine

Sphingosine, the simplest sphingolipid, is an amphiphilic molecule found in the plasma membrane in nearly all mammalian cells and serves as an important part of the biophysical structure of cells as well as an important mediator of cell signaling. Although the antimicrobial properties of sphingosine and other sphingolipids were published in 1948, it was not until recently that sphingosine was identified as an important part of mammalian innate defense against bacterial invasion, specifically via epithelial surfaces in contact with the external environment (i.e., respiratory, genitourinary, gastrointestinal tracts).

Further studies were published as a result of research conducted on lipids of the skin in 1992 which identified sphingosine and similar molecules as the key antimicrobial lipids in the skins' lipid antibacterial defense. More recently, sphingosine was identified as a potential therapeutic agent for skin infections, and sphingosine has emerged as an important agent in the oral and dental health practices for its effectiveness against oral pathogens.

U.S. Patent Publication No. US20150147361 discloses the use of coatings comprising sphingosine related compounds for inhibition of erosion/decay of hydroxyapatite (HAP) surfaces, including bone/teeth. The investigators further postulated that such coatings could be effective for inhibiting biofilm formation on medical devices. The coatings of the '361 publication, however, were limited to aqueous-based solutions of phytosphingosine, and relied on the addition of hydroxyapatite nanoparticles for proper adhesion to non-HAP surfaces. The adsorption model for phytosphingosine to HAP describes a monomolecular adsorption layer in which additional adsorption after the monomolecular layer is formed is limited or impossible due to critical micelle concentration. The thickness, applicability, and efficacy of the coatings is therefore limited. Notably, the '361 examples are limited to extremely sparse monomolecular coatings formed from aqueous solutions of phytosphingosine and fail to exemplify coatings suitable for any surface other than HAP surfaces.

Thus, there remains a persistent need in the art for effective and safe coatings for the inhibition of bacteria adhesion and biofilm formation, in particular on implantable biomaterials in a medical health context.

SUMMARY

Accordingly, embodiments of the invention provide novel sphingolipid coatings, methods for making the coatings, and methods with demonstrated efficacy for preventing adherence of multiple species of bacterial cells and for inhibiting formation of biofilm on a variety of substrate surfaces.

One embodiment is directed to methods for applying a sphingolipid aggregate coating to a surface of a substrate, the methods comprising: suspending an amount of sphingolipid in a fast-evaporating or medium-evaporating organic solvent;

applying energy to the suspension sufficient to create a colloidal dispersion of sphingolipid in the solvent; heating the dispersion sufficient to create a solution; and coating the surface of the substrate with at least one application of solution, each application followed directly by a solvent evaporation period. Non-limiting examples of suitable sphingolipids include sphingosine, sphinganine, phytosphingosine, psychosine and derivatives thereof. The use of fast/medium-evaporating solvents is critical to achieving a desired aggregate architecture and thickness; although means for enhancing evaporation may also be utilized when either fast or medium-evaporating solvents are used.

Another embodiment is directed to the novel Sphingolipid coatings formed according to embodiments of the inventive processes. The coatings are distinguishable from coatings known in the art due to the self-assembly of the sphingolipid in the solvent upon deposition on the substrate surface and drying, at each round of coating, and the aggregate form, architecture, and thickness thereby achieved.

Another embodiment is directed to medical devices coated with a sphingosine coating formed from coating the device in a solution of sphingosine in hexane, acetone or ethanol wherein coating comprises at least one step comprising coating followed directly by substantially evaporating residual hexane.

Another embodiment is directed to medical devices coated with a phytosphingosine coating formed from applying at least one coating to the device of a solution of phytosphingosine in acetone or ethanol, wherein a coating step is followed directly by substantially evaporating residual acetone or ethanol.

Broadly, embodiments provide methods for preventing or inhibiting the formation of a biofilm on a substrate by coating the substrate with a coating according to an embodiment of the invention as described in detail herein.

These and other embodiments and aspects will be further understood and clarified by reference to the figures and detailed description below. Although certain embodiments are illustrated and explained by specific examples, a person of ordinary skill in the art will understand that such examples should not be construed as limiting the full scope of the invention as set forth in the appended claims.

BRIEF DESCRIPTION OF THE FIGURES

FIG. 2A) images comparing hexane-coated surface plating and SPH-hexane-coated surface plating after incubation in *A. baumannii* and removal of nonadherent bacteria; 2B) microfocal images comparing hexane-coated surface plating and SPH-hexane-coated surface plating after incubation in *P. aeruginosa* and removal of nonadherent bacteria.

FIG. 4) images comparing acetone-coated and phytosphingosine/acetone-coated platings after incubation in *A. baumannii* and removal of nonadherent bacteria.

FIG. 5) tabled results for adherent bacterial counts showing phytosphingosine/acetone coating applied to a PVC endotracheal tube and pieces of aluminum tested against *Staphylococcus aureus, Pseudomonas aeruginosa*, and *Acinetobacter baumannii* bacterial strains.

FIG. 7) tabled results for adherent *P. aeruginosa, S. aureus* and *A. baumannii* bacteria counts for phytosphingosine-coated versus control (ethanol) coverslips.

FIG. 9A) thin-film confocal microscopy image of glass slide after dip-coating once with hexane alone; 9B) thin-film confocal microscopy image of glass slide after dip-coating once with sphingosine/hexane coating solution; 9C) thin-film confocal microscopy image of glass slide after dip-coating 2× with sphingosine/hexane coating solution; 9D) thin-film confocal microscopy image of glass slide after dip-coating 3× with sphingosine/hexane coating solution; 9E) thin-film confocal microscopy image of glass slide after dip-coating 4× with sphingosine/hexane coating solution.

FIG. 14A) bar graph showing in vitro bacterial adherence of AB, PA, and MRSA to vehicle (ethanol)-coated vs. phytosphingosine-coated plastic coverslips after one application of bacterial suspension growth media followed by 24 hours incubation; 14B) after four applications of bacterial suspension at 0, 24, 48 and 72 hours followed by 12 hours incubation.

DETAILED DESCRIPTION

Embodiments of the invention provide coating solutions of a sphingolipid dissolved in a fast- or medium-evaporating solvent, and novel coating processes, and novel coatings that may be applied to a variety of substrates to substantially prevent adherence of bacteria and/or formation of biofilms on the substrate. Biofilm, as used herein, is a term of art referring to an aggregate of microorganisms in which cells adhere to each other and/or to a surface and are frequently embedded within a self-produced matrix of extracellular polymeric substance.

According to one embodiment, methods for applying a sphingolipid aggregate coating to a surface of a substrate are provided. A "substrate" may be any substrate on which it is desirable to prevent or inhibit the adherence of bacteria and/or the establishment of biofilms. Non-limiting examples of suitable substrates include non-porous substrates such as plastic, textile, glass, leather, painted or varnished surfaces, marble, granite, and other natural or synthetic rock/tile materials, processed wood and metal. Some porous substrates may also be suitable for coating according to embodiments of the invention, including cardboard, paper, clay, and untreated wood. Although aspects of the invention are discussed and exemplified using specific substrates, it will be readily apparent to a person of ordinary skill in the art that any surface on which biofilm formation is sought to be inhibited/prevented may be a suitable substrate. In particular, surfaces involved in heating ventilation, air conditioning systems, and filters for use therein may be coated in accordance with inventive embodiments.

Figure 12:
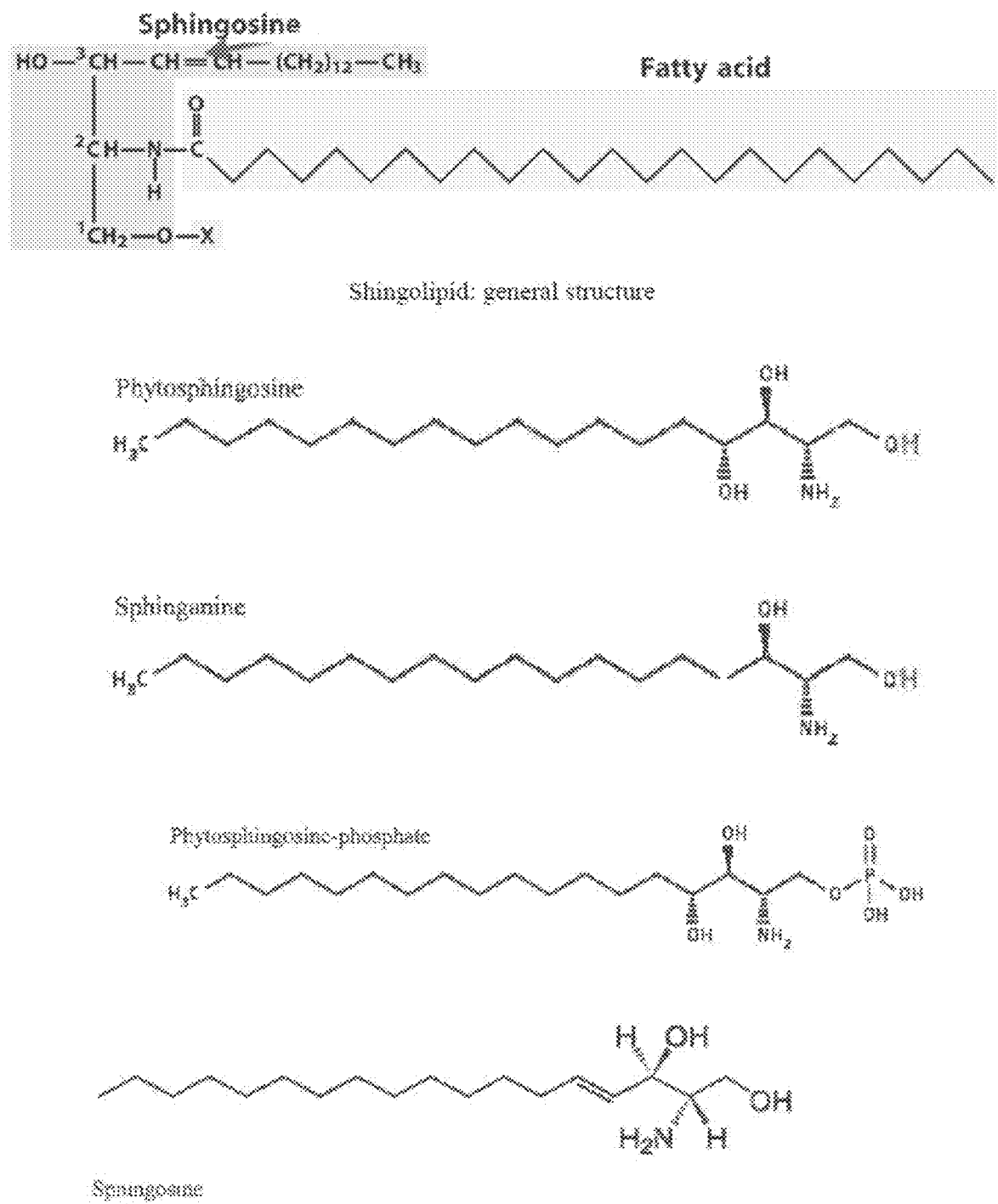
FIG. 12) representative sphingosine compounds for use in embodiments of the invention.

A "sphingolipid" as referred to herein includes any member of a class of lipids containing the organic aliphatic amino alcohol sphingosine or a substance structurally similar to it. Among the most simple sphingolipids are the ceramides (sphingosine plus a fatty acid). Non-limiting exemplary sphingolipids are set forth structurally in FIG. 12. Nonionic derivatives of specific sphingolipids are contemplated as within the scope of the invention. Sphingolipids are amphiphilic molecules with a hydrophilic headgroup and at least one hydrophobic chain, and are classified generally as nonionic surfactants. According to specific embodiments, the sphingolipid is selected from one or more of sphingosine, sphinganine, phytosphingosine, psychosine, and non-ionic derivatives thereof. In more specific embodiments, non-ionic derivatives are selected from D-erythro-sphingosine and D-ribo-Phytosphingosine 4-hydroxysphinganine.

A surfactant "aggregate" as utilized herein is a supramolecular assembly of surfactant molecules. Surfactant aggregates have different shapes depending on molecular parameters (such as curvature of aggregate surface and the packing parameter) of the surfactant and system variables such as concentration and temperature. Common surfactant aggregate architectures in traditional solvents include micelles (spherical, rod-like, worm-like, bilayer, and cylindrical), microemulsions, liquid crystals (lamellar, hexagonal and cubic), vesicles and gel.

The surfactant aggregates formed upon self-assembly in organic solvents have come under recent scrutiny for their unique architectures (see, e.g. Tadros, et al. "Self-organized surfactant structures" WILEY-VCH Verlag Gmbh & Co. KGaA, 2011, and Shrestha, L. K. et al. 'Structure of Non-ionic Surfactant Micelles in Organic Solvents" J Phys Chem B 2009 May; 113 (18): 6290-8, the entire disclosures of which are incorporated herein by this reference). The present investigators discovered that subjecting aggregate suspensions to conditions which result in solubilizing the sphingolipid in a fast/medium-evaporating solvent, provides a coating solution that may be applied singly or in serial layering/drying protocols. The resultant coating comprises sphingolipid aggregates bound to the coated surface in a highly concentrated form. The resultant coatings are shown herein to be resistant to bacterial adhesion and formation of biofilms for a variety of substrates.

According to some embodiments, an amount of sphingolipid is suspended in a fast or medium-evaporating organic solvent. A solvent according to embodiments of the invention includes any organic solvent with a fast evaporation rate, and some solvents with a medium evaporation rate when subjected to evaporation enhancing/drying conditions. Evaporation rate is the rate at which a material will vaporize (evaporate, change from liquid to vapor) compared to the rate of vaporization of a specific known material under ambient conditions. This quantity is a ratio; therefore it is unitless. A fast-evaporating solvent, as the term is utilized herein, conforms to a conventional industry definition as one with an evaporation rate of 3.0 (three time the evaporation of normal butyl acetate), such as acetone (5.6), hexane (8.3), or methyl ethyl ketone or MEK (3.8). Chemicals with evaporation rate between 0.8 and 3.0, such as ethyl alcohol (1.4) or VM&P naphtha (1.4) are classified as medium evaporating. Chemicals with evaporation rates less than 0.8, such as water (0.3), mineral spirit (0.1), or xylene (0.6) or isobutyl alcohol (0.6) are classified as slow evaporating and are not contemplated as within the scope of the invention. In accordance with embodiments of the invention, the rapid evaporation of the solvent subsequent to a coating step is critical to achieving the desired aggregate assembly of the sphingolipid. Preferred organic solvents are therefore those with a standard evaporation rate greater than 3. According to specific embodiments, the fast-evaporating solvent is selected from one or more of hexane, acetone, cyclohexane, and methyl ethyl ketone. In very specific embodiments, the sphingolipid comprises a sphingosine and the solvent is hexane. In other very specific embodiments the sphingolipid comprise phytosphingosine and the solvent comprises acetone.

According to some embodiments, however, the evaporation rate of high-to-medium or medium evaporating solvents, such ethanol, may be enhanced, such as by air drying, blow-drying, vacuum-drying or heat-assisted drying, with retention of desired coating properties. According to one specific embodiment, the sphingolipid comprises sphingosine and the solvent comprises ethanol, which is subject to blow-drying and/or elevated temperature during the evaporation aspect of the coating cycles. The evaporation rate of organic solvents is a well known parameter and may be readily ascertained by reference to, for example, Handbook of Organic Solvent Properties, Halsted Press as an imprint of John Wiley & Sons Inc., 605 Third Avenue, New York, NY 10158, Smallwood, 1996, the entire disclosure of which is incorporated herein.

Energy is then applied to the suspension sufficient to create a colloidal dispersion of the sphingolipid in the solvent. Energy may be in the form of mechanical energy, sonication, heating, and combinations thereof. In specific embodiment, a probe or bath sonicator is employed. In very specific embodiments the sonicator is employed at ultrasonic frequencies, and in other specific embodiments the sonication frequency is between 20 kHz and 40 kHz. According to some specific embodiments the temperature of a bath sonicator is set to at least 5-10° C. below the selected solvent's boiling point. In very specific embodiments the temperature of the bath is set at 5° C. below the solvent's boiling point. Heating is to a temperature less than the solvent's boiling point. According to more specific embodiments, the suspension is heated to within 10° C. of the solvent boiling point and sonicated at about 40 kHz. According to specific embodiments, a resulting colloidal dispersion comprises sphingolipid and/or sphingolipid aggregates in a dispersed phase having a size between 1 nm and 1 μm. The colloidal dispersion is heated for an amount of time sufficient to result in a solution of the sphingolipid in the solvent. Generally, this point may be ascertained by observing an absence of visual aggregates in the solution. The resultant solution provides the coating solution.

Desired substrates are coated by any suitable coating methods including any method which employs rapid evaporation of solvent, for example, spray coating, spin coating, and dip coating. Generally, methods which involve the formation of concentration gradients during the coating process leading to "skins" that inhibit evaporation are not utilized. Without being bound by theory, the present investigators surmise that the self-assembly of the sphingolipid on the surface of the substrate is guided by the solvent and rapid evaporation freezes the resultant architecture in place. A single coating may be effective for preventing adherence of bacterial cells; however in some embodiments durability and sustained efficacy may be enhanced by multiple coatings. Thus, according to some embodiments, the surface of the substrate is coated with at least one application of solution, each application followed directly by a solvent evaporation period. As utilized herein, an "application cycle" includes both a coating step and an evaporation step. An evaporation step results in substantially complete evaporation of residual solvent. Evaporation is substantially complete if the coated substrate is dry to the touch. According to other embodiments, at least ten application cycles are provided. In other specific embodiments, 2, 3, 4, 5, 6, 7, 8, 9, or 10 application cycles are provided. The number of application cycles may vary by the specific combination of sphingolipid and solvent, the drying conditions if on-site, by quality of the substrate, and by the intended environment/use of the coated substrate.

Another embodiment of the invention is directed to the coatings formed from embodiments of the inventive processes. As demonstrated in FIG. 9B through FIG. 9F, the superarchitecture of the coating changes with each additional coating application (dip). The high concentration of sphingolipid aggregates across the substrate surface provides the unexpectedly effective inhibition of bacteria adherence to the coated surface.

VAP continues to be a major cause of morbidity and mortality in critically ill patients. While prompt diagnosis and effective treatment with standard antibiotic regimens is important in mitigating the detrimental effects of VAP, development and implementation of more effective prevention strategies will decrease the incidence and likely provide a greater reduction in morbidity and mortality. Low cost strategies such as semi-recumbent positioning, chlorhexidine oral care, and subglottic suctioning have all been shown to reduce rates of VAP, and studies have shown they have been successfully implemented in community systems (Youngquist et al. 2007). Silver-coated endotracheal tubes have also been shown to reduce rates of VAP, but have not shown widespread implementation, possibly secondary to the large cost associated with silver-coated tubes.

The cause of VAP is likely multifactorial, but the presence of a biofilm that develops after only 24 hours of tracheal intubation has been identified as a likely source of infection (Gil-Perotin et al. 2012; Vandecandelaere et al. 2013). A safe antimicrobial coating that can prevent bacterial adherence, the first step in biofilm formation, that can be applied easily and for a low cost has the potential to affect meaningful change in prevention of VAP. Sphingosine is a sphingolipid found in the membranes of most eukaryotic cells. Administration via inhalation was shown not only to reduce rates of pneumonia in susceptible mice, but also did not result in any observable toxicity (Pewzner-Jung et al. 2014). Sphingosine and phytosphingosine have been shown to have antimicrobial activity against both gram positive and gram negative bacteria. Additionally, sphingosine's presence in the skin, oral mucosa, and respiratory mucosa suggests sphingosine is a part of mammalian innate immunity. Thus, it is likely that sphingosine's antimicrobial mechanism is not prone to development of bacterial resistance.

Embodiments of the evaporative-induced deposition of sphingosine via dip coating provide a simple and cheap way to apply a biologically significant amount of sphingosine on the surface of endotracheal tubes. According to some method embodiments, only a single dip is required and thus only a very small volume of sphingolipid solution is used.

The following Examples establish that sphingosine-coated and phytosphingosine-coated endotracheal tubes are highly efficacious at preventing bacterial adherence against at least three of the most common pathogens, AB, PA, and SA, associated with VAP when compared with standard plasticized PVC endotracheal tubes. Additionally, the data establishes that sphingolipid-coated tubes are at least equally efficacious as silver-coated endotracheal tubes.

EXAMPLES

The following examples are intended to illustrate specific features and aspects of the invention and should not be construed as limiting the scope thereof.

With respect to the following examples, D-erythrosphingosine (d18:1) and D-ribo-phytosphingosine were purchased from Avanti Polar Lipids (Alabaster, AL). Hexane (anhydrous, 95%) and Acetone (>99.9%) were purchased from Sigma-Aldrich. Absolute, 200 proof, molecular biology grade ethanol was purchased from Fisher Scientific (Pittsburgh, PA). Plasticized polyvinyl chloride (PVC) endotracheal tubes (8.0 mm) were purchased from Cardinal Health (Dublin, OH). Silver-coated endotracheal tubes (8.0 mm) were purchased from Bard Medical (Covington, GA). Plastic coverslips (24×60 mm) were purchased from Electron Microscopy Sciences (Hatfield, PA). Three different bacterial strains were used: Methicillin-Resistant *Staphylococcus aureus* (USA 300), *Acinetobacter baumannii*, and *Pseudomonas aeruginosa* (ATCC).

Mean bacterial counts (cfu) are calculated and reported +/−standard deviation. Mean bacterial counts from sphingosine-coated, phytosphingosine-coated, and silver-coated endotracheal tube segments are compared to vehicle-coated segments and silver-coated segments using Student's t test in Microsoft Excel for Mac 2011.

Example 1

This example illustrates one process embodiment for making a sphingosine coating, and demonstrates efficacy in inhibition of biofilm formation on a sphingosine-coated PVC substrate.

1. D-erythro-sphingosine was dissolved in reagent grade hexane to a concentration of 25 mM in a 100 mL glass bottle with a screw cap;
2. The sphingosine/hexane suspension was sonicated in a bath sonicator at 37° C. for 10 minutes;
3. heated to a temperature of 50° C. until sphingosine aggregates were no longer visible indicating that sphingosine was completely dissolved in the solvent;
4. endotracheal tubes were dip-coated by placing the tube into the sphingosine solution and immediately withdrawing;

5. residual hexane was allowed to completely evaporate (4 minutes);
6. steps 4 and 5 were repeated for a total of 10 times.

PVC coverslips were coated with either sphingosine/hexane or hexane alone and incubated in bacteria for 12 hours, washed to remove nonadherent bacteria, and sonicated to release adherent bacteria for plating to quantify bacterial load.

Figure 1A:
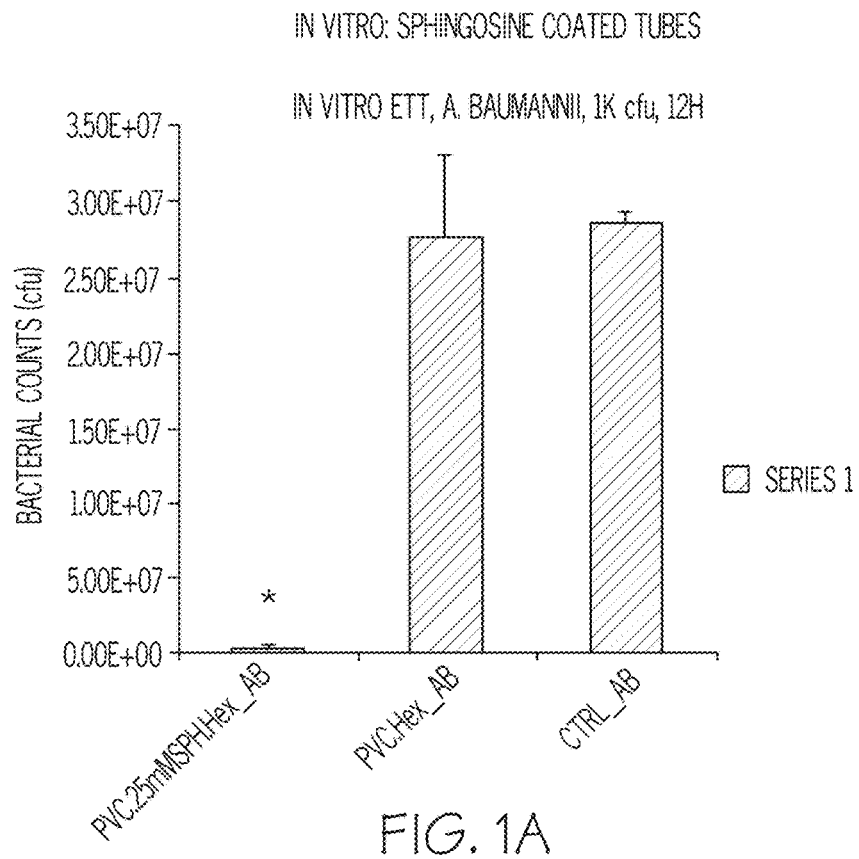
FIG. 1A) graphical representation comparing *A. baumannii* bacteria counts on PVC-coated substrate coated with SPH-hexane, hexane, and control; 1B) graphical representation comparing *P. aeruginosa* bacteria counts on PVC-coated substrate coated with SPH-hexane, hexane, and control; 1C) graphical representation comparing *S. aureus* bacteria counts on PVC-coated substrate coated with SPH-hexane, hexane, and control.
Figure 1B:
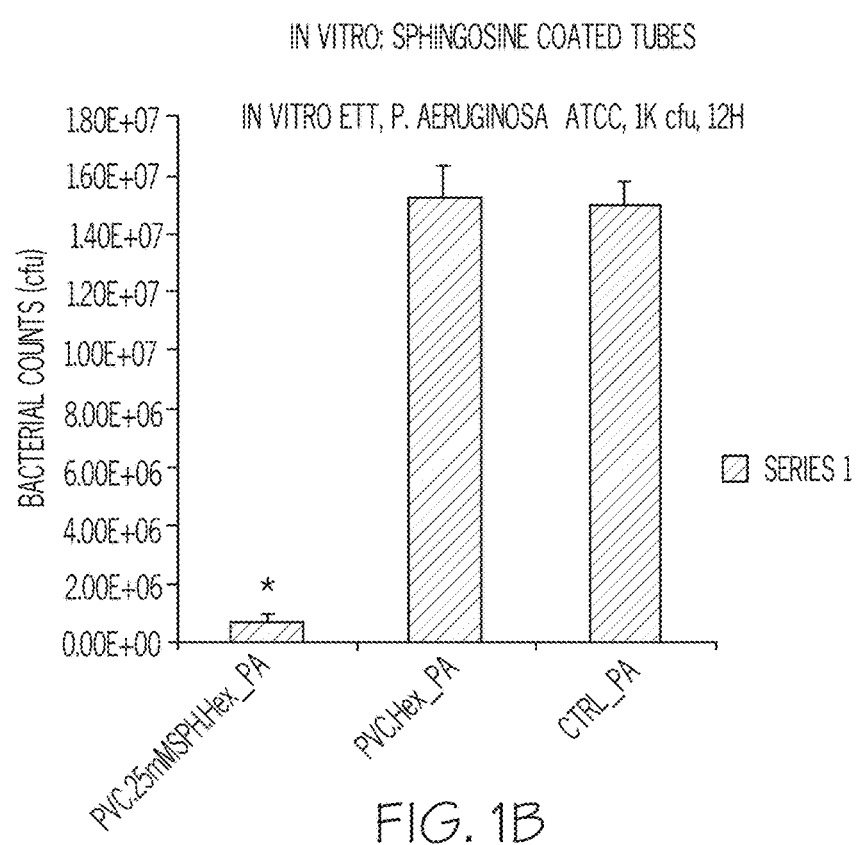
Figure 1C:
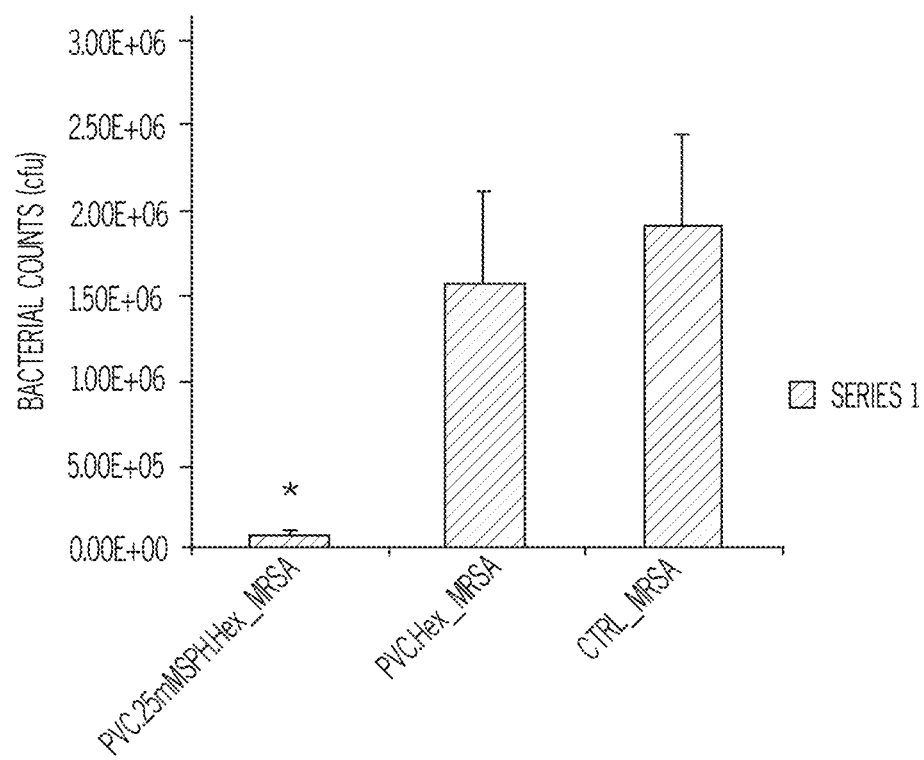

Bacterial counts (*A. baumanii*, P. (FIG. 1A) *aeruginosa* ATCC (FIG. 1B), methicillin resistant *S. aureus* (FIG. 1C) on the slips were calculated and plotted for the sphingosine/hexane coating (S/H), hexane only (H), and no coating (C). *A. baumannii* counts showed a 2.1 log reduction (99.2%) (FIG. 2A), *P. aeruginosa* counts showed a 1.3 log reduction (95.3%) (FIG. 2B) and *S. aureus* counts showed a 1.5 log reduction (96%) for the S/H over H.

Example 2

This example illustrates a process embodiment for making a phytosphingosine coating, and demonstrates efficacy in inhibition of biofilm formation on phytosphingosine-coated ETTs.
1. D-ribo-Phytosphingosine 4-hydroxysphinganine is dissolved in reagent grade acetone to a concentration of 30 mM in a 100 mL glass bottle with a screw cap;
2. The phytosphingosine/acetone suspension is sonicated in a bath sonicator at 43° C. for 10 minutes; phytosphingosine aggregates were completely dissolved;
3. Endotracheal tubes were dip-coated and immediately withdrawn;
4. residual acetone was completely evaporated, aided by a directed air stream;
5. steps 3 and 4 were repeated for a total of 5 times.

Figure 3:
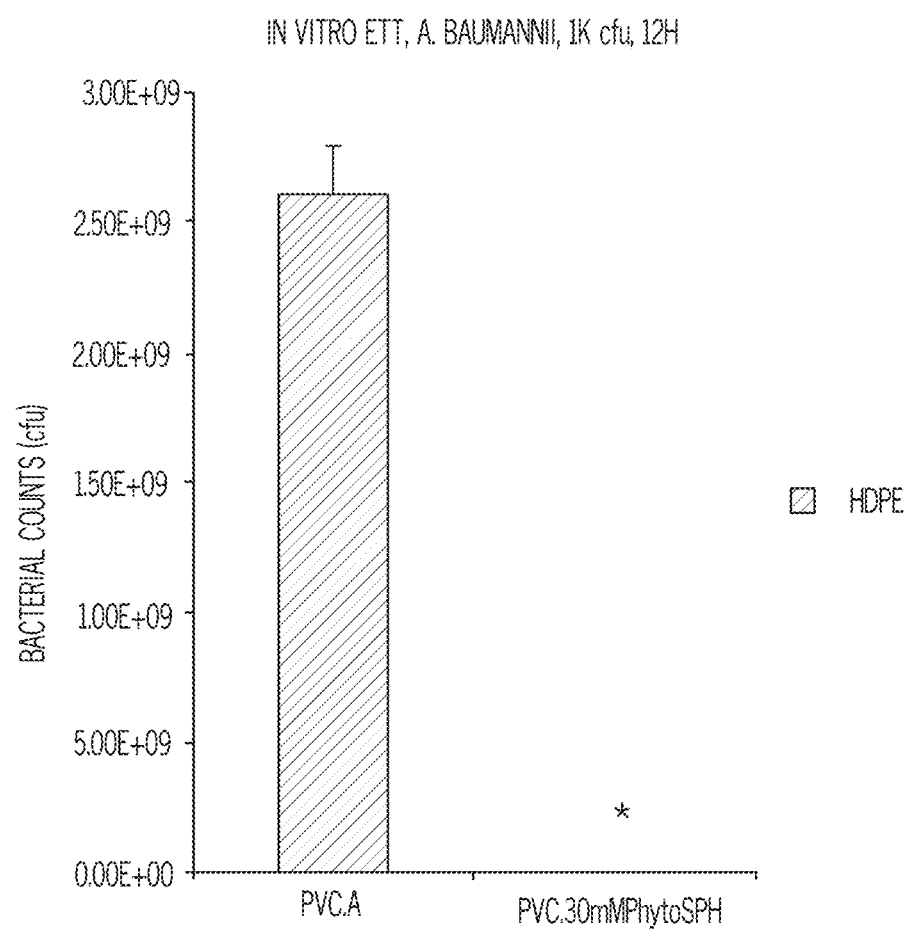
FIG. 3) graphical representation of data comparing *A. baumannii* bacteria counts for PVC coated with acetone to PVC coated with phytosphingosine-acetone coating.
Figure 6A:
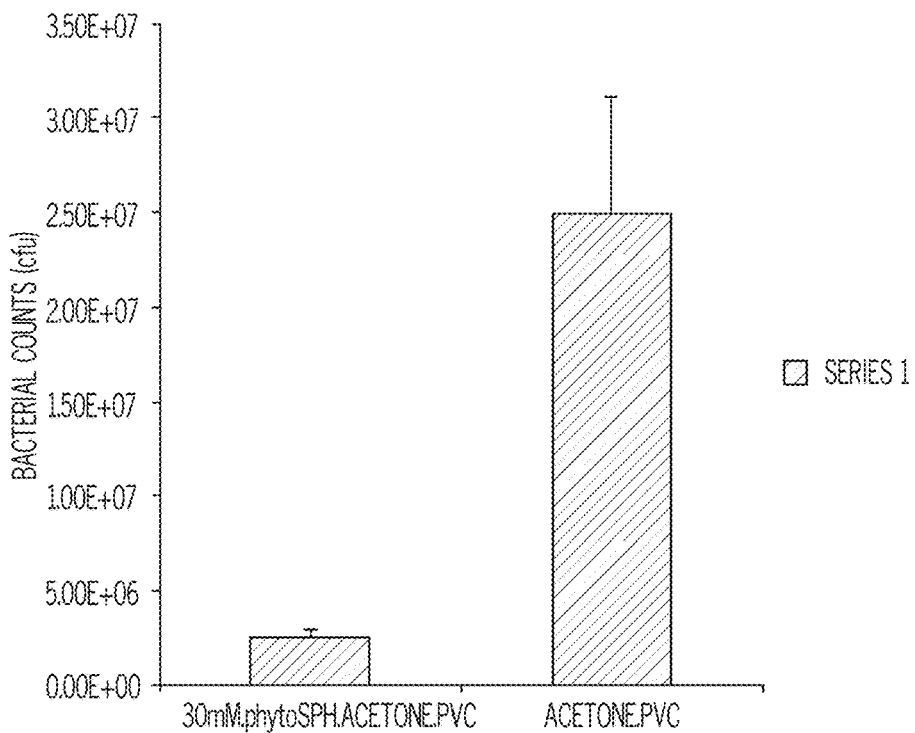
FIG. 6A) graphical representation of adherent *P. aeruginosa* bacteria count on coated versus control PVC; 6B) graphical representation of adherent *P. aeruginosa* bacteria count on coated versus control aluminum; 6C) graphical representation of adherent *S. aureus* bacteria count on coated versus control PVC; 6D) graphical representation of adherent *S. aureus* bacteria count on coated versus control aluminum; 6E) graphical representation of adherent *A. baumannii* bacteria count on coated versus control PVC; 6F) graphical representation of adherent *A. baumannii* bacteria count on coated versus control aluminum.
Figure 6B:
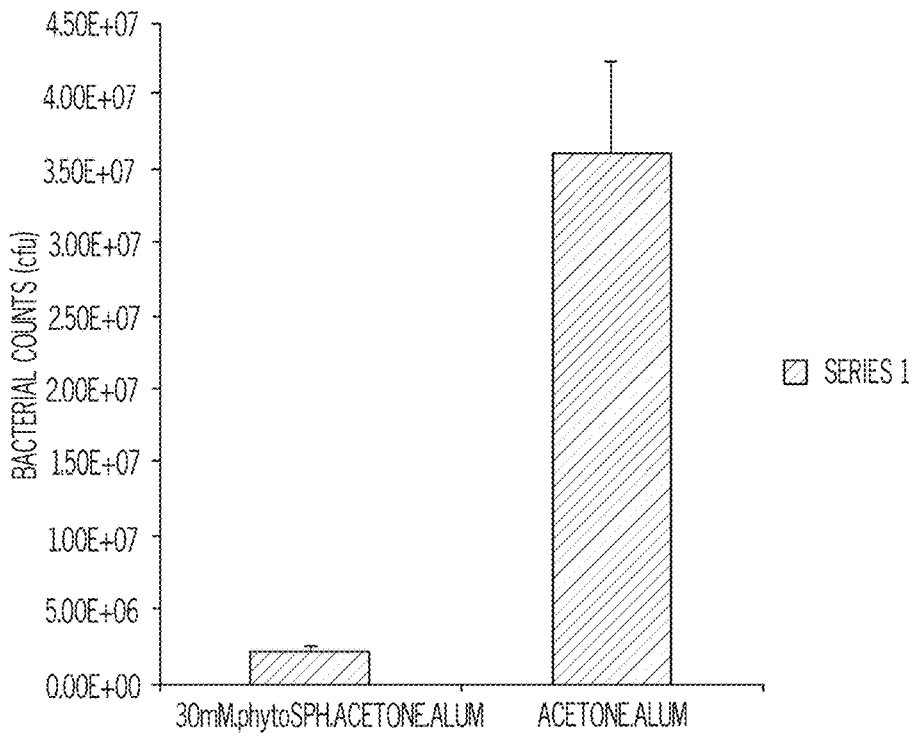
Figure 6C:
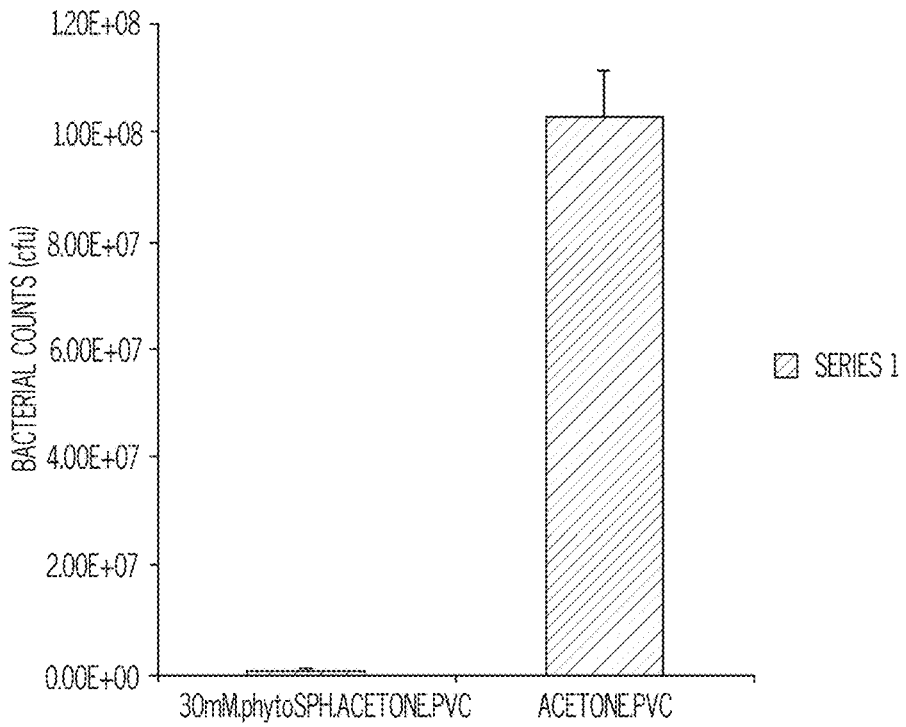
Figure 6D:
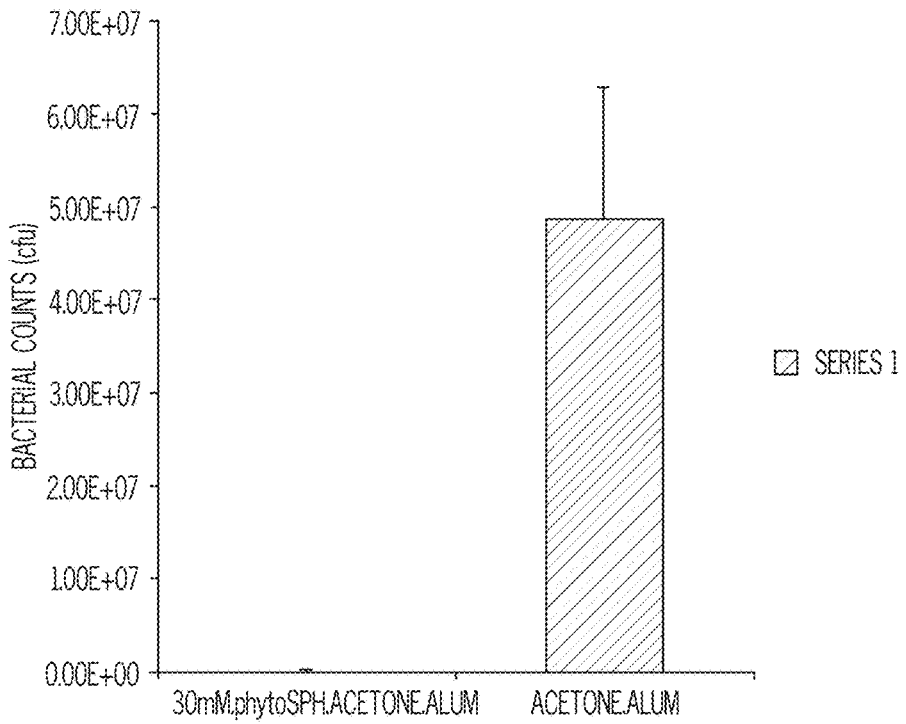
Figure 6E:
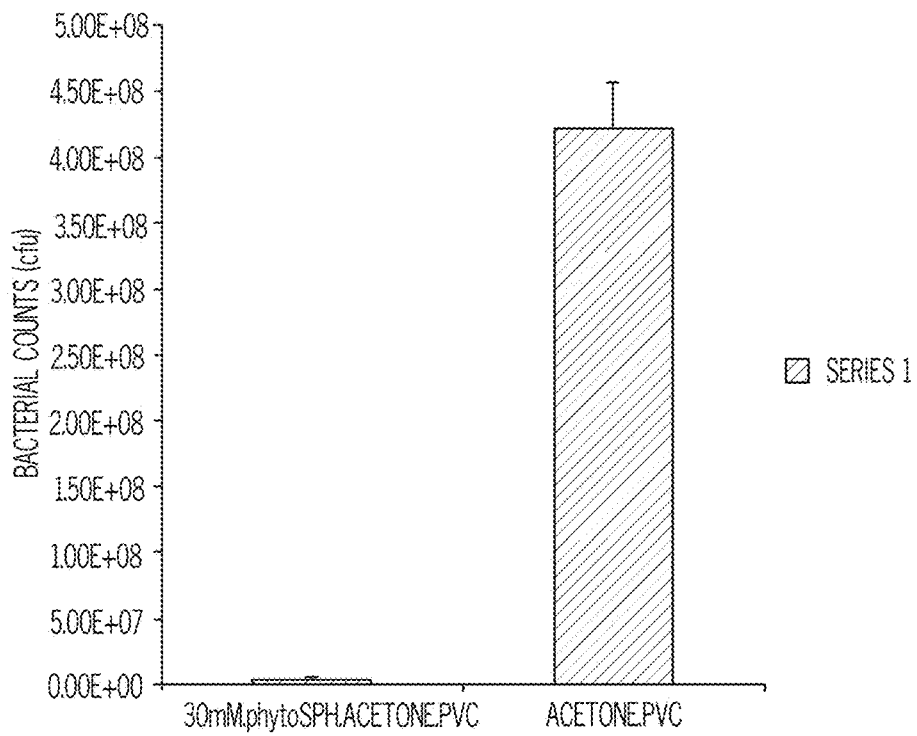
Figure 6F:
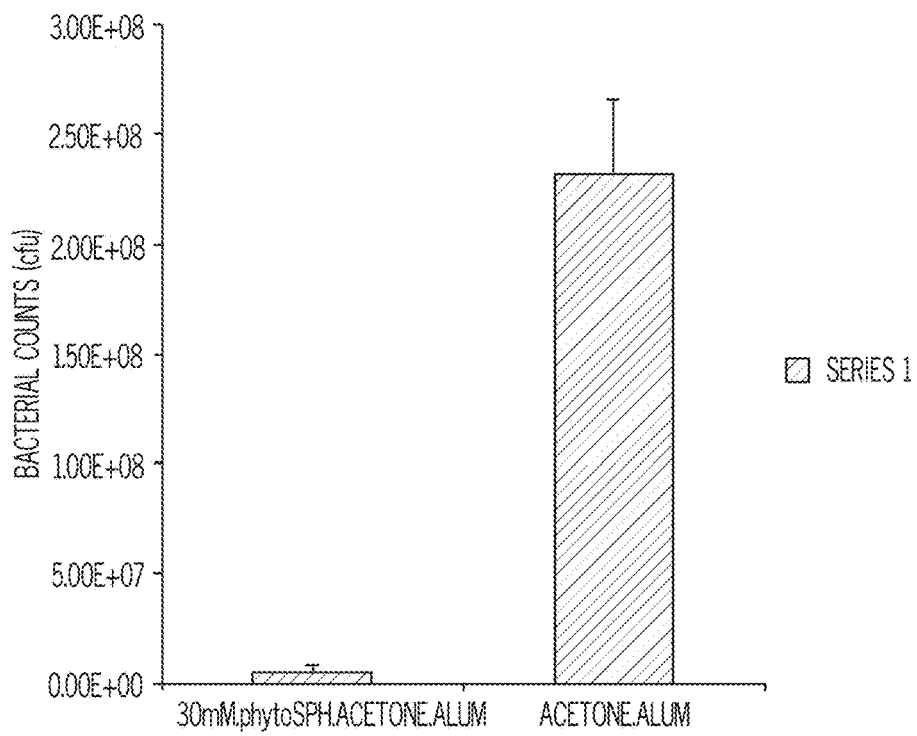

*A. baumannii* bacterial counts were taken after 12 hours and results are shown graphically in FIG. 3. The counts showed a 3.29 log reduction (99.95%) for the phytosphingosine/acetone coated tube over the acetone-coated tube. Photographs of bacteria for acetone versus phytosphingosine/acetone are compared in FIG. 4.

Example 3

This example illustrates efficacy of a phytosphingosine/acetone coating applied to a PVC endotracheal tube and pieces of aluminum tested against *Staphylococcus aureus*, *Pseudomonas aeruginosa*, and *Acinetobacter baumannii* bacterial strains.

Solvent-coated and phytosphingosine-coated pieces of ETT and aluminum were incubated in bacteria for 12 hours, washed to remove non-adherent bacteria, and the pieces were sonicated to release adherent bacteria from the surface, which were plated to quantify bacterial load.

The tabled results are set forth as FIG. 5 and the comparative graphical representations are set forth in FIGS. 6A-6F.

Example 4

This example illustrates efficacy of a phytosphingosine/ethanol coating applied to PVC coverslips against Methicillin resistant *Staphylococcus aureus*, *Pseudomonas aeruginosa*, and *Acinetobacter baumannii* bacterial strains.

Solvent-coated and phytosphingosine-coated coverslips were incubated in bacteria for 24 hours and washed to remove nonadherent bacteria. Coverslips were incubated another 6 hours at 37° C. to allow water to evaporate and to force remaining bacteria to contact the solvent or PhySPH-coated surface. Coverslips were then sonicated to release adherent bacteria and plating was done to quantify bacterial load.

Figure 8:
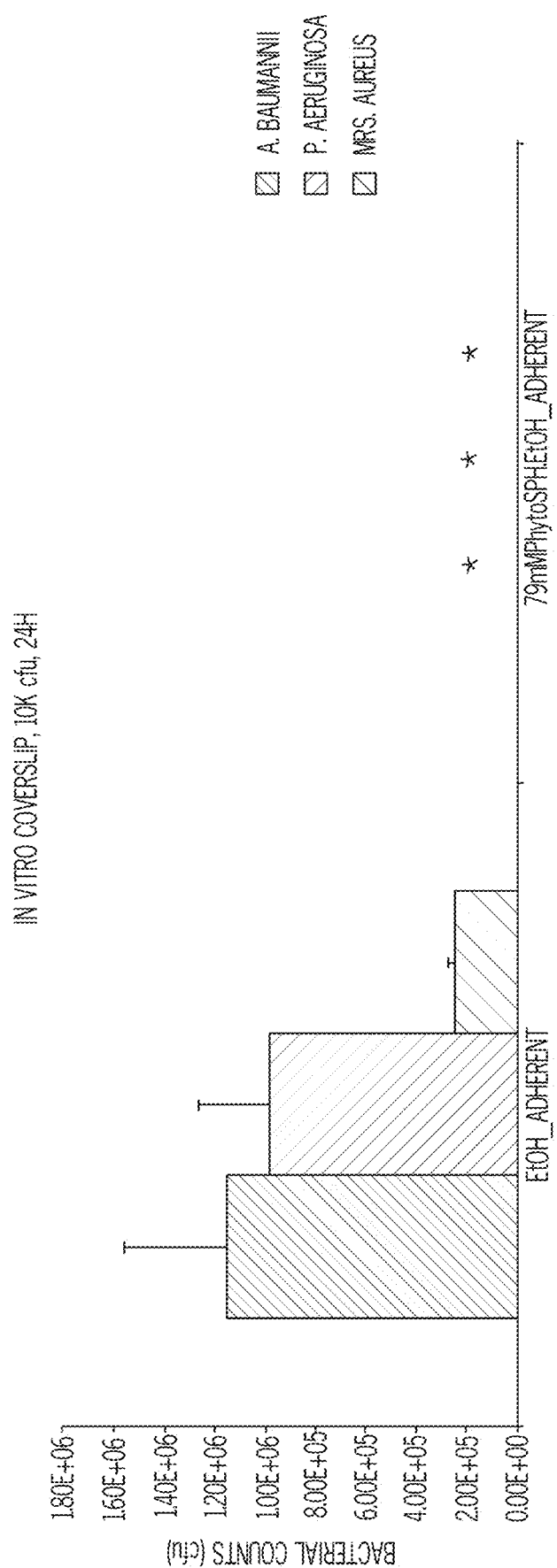
FIG. 8) bar graph summary of data for adherent *P. aeruginosa, S. aureus* and *A. baumannii* bacteria counts for phytosphingosine-coated versus control (ethanol) coverslips.

The tabled results are set forth as FIG. 7, and the graphical representation is set forth as FIG. 8.

Example 5

This example provides visualization of the coating formed on a glass substrate from a coating process embodiment. Images were obtained via confocal microscopy in which a 100× objective was used and Z stacks were obtained through the sample. Glass slides are coated with a sphingosine-hexane coating solution according to embodiments of the invention. The slides were dip-coated, allowed to dry, then stained with Syto 9 in DMSO. FIG. 9A is a control image of hexane alone. FIGS. 9B through 9E are images taken after 1 dip, 2 dips, 3 dips, and 4 dips, respectively, in the sphingosine-hexane coating solution. As can be seen, the coating is comprised of aggregates rather than a monomolecular layer of sphingosine.

Example 6

Figure 10A:
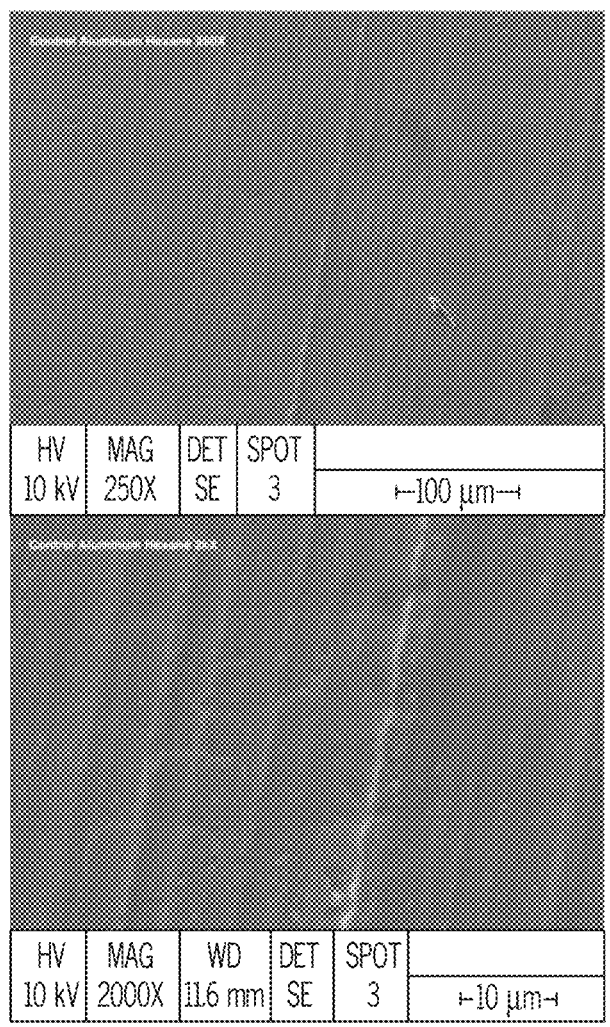
FIG. 10A) image obtained by electron microscopy of 1-dip hexane control coated aluminum at 250× and 2000× magnifications; 10B) image obtained by electron microscopy of 1-dip sphingosine-hexane coated aluminum at 250× and 2000× magnifications.
Figure 10B:
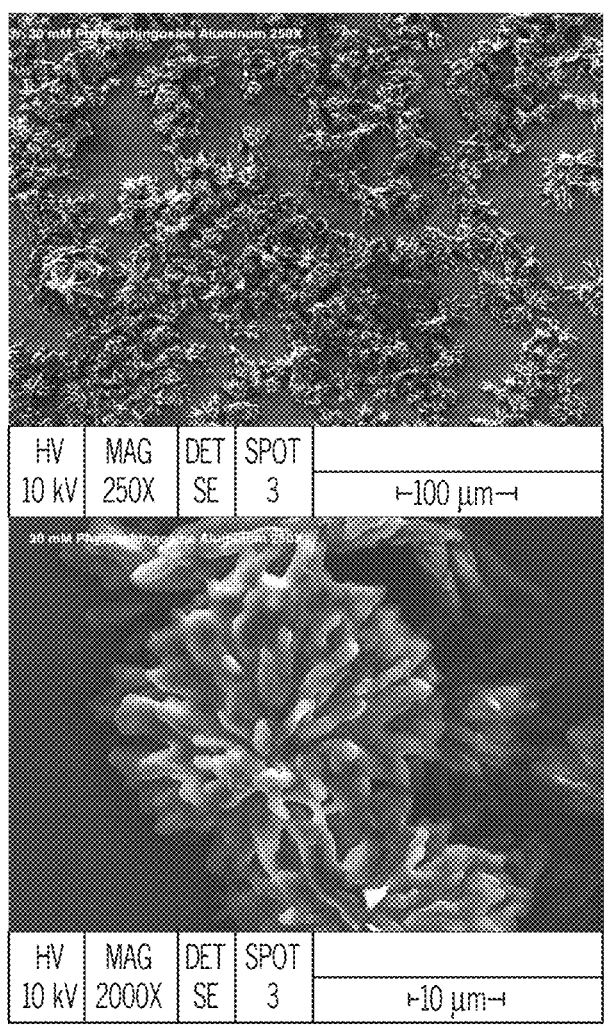
Figure 11:
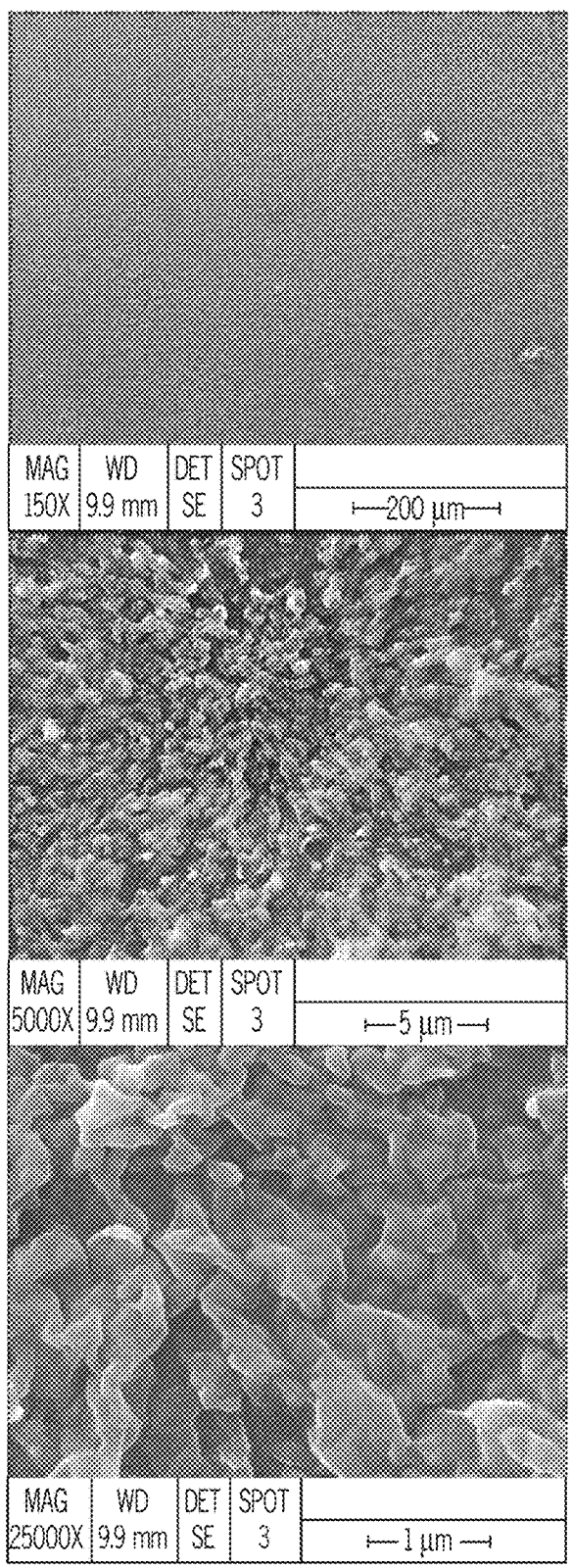
FIG. 11) series of electron microscopic images of magnifications (150×, 5000×, 25,000×) of a sphingosine-hexane coating on a PVC substrate.

This example provides visualization of the coating formed on an aluminum substrate and on a PVC substrate (ETT) from a coating process embodiment. A sphingosine-hexane coating solution was made and the aluminum and ETT pieces were dip-coated, allowed to dry, stained with osmium tetroxide, allowed to dry, and sputter-coated with gold plasma. Images were obtained via electron microscopy. FIG. 10A is an image of the hexane control coated aluminum at 250× and 2000×, and FIG. 10B is an image of the sphingosine-hexane coated aluminum at 250× and 2000×. FIG. 11 is an image series of magnifications (150×, 5000×, 25,000×) of a sphingosine-hexane coating on a PVC substrate.

Example 7

This Example illustrates one embodiment of evaporative-induced deposition of sphingolipids.

Sphingolipid solutions were prepared by dissolving either sphingosine or phytosphingosine into organic solvents (i.e. hexane, acetone, or ethanol). The concentration of sphingosine in hexane was 30 mM. Sphingosine was added to hexane which was preheated to 60° C. in a water bath. After addition of sphingosine, the solution was agitated and sonicated until the sphingosine aggregates were no longer visible and the solution was clear. Phytosphingosine (30 mM) in acetone and sphingosine (80 mM) and phytosphingosine (80 mM) in ethanol were prepared similarly with different heating temperatures. The preheated temperatures were 50° C. and 70° C. for acetone and ethanol, respectively.

Both endotracheal tube segments and plastic coverslips were used as coating substrates. Endotracheal tube segments were prepared by cutting 1 cm long sections of endotracheal tubes. Full length plastic coverslips were utilized. Sphingolipid thin films were deposited onto the surface of endotracheal tubes and plastic coverslips by dip coating the object into a heated sphingolipid solution. The tube segments were manipulated using a 1 mL insulin needle stuck through the plastic and the coverslips were manipulated using straight Kelly forceps. The tube segments/coverslips were immersed into the solution for 1 s, and then slowly withdrawn at a rate of 1 cm/second. Evaporative-induced deposition of the thin film occurred upon subjecting the object to room temperature atmosphere. The plastic coverslips were less resistant to acetone and began to dissolve when dip coated, thus 100% ethanol replaced acetone as the solvent. Repeated dips of up to 10 times were utilized initially (FIG. 13) but coating optimization with ethanol as solvent was achieved with one dip (FIGS. 14-21).

Example 8

This Example illustrates determination of inhibition of bacterial adherence using a modified version of the in vitro biofilm colonization model developed by Kuhn et al. (Kuhn, D. M. et al., 2002. Antifungal susceptibility of *Candida* biofilms: unique efficacy of amphotericin B lipid formulations and echinocandins. *Antimicrobial Agents and Chemotherapy*, 46 (6), pp. 1773-1780) and utilized by Raad et al. (Raad, I. I. et al., 2011. The prevention of biofilm colonization by multidrug-resistant pathogens that cause ventilator-associated pneumonia with antimicrobial-coated endotracheal tubes. *Biomaterials*, 32 (11), pp. 2689-2694). The entire disclosures of these references are incorporated herein.

Bacteria were grown overnight on trypticase soy agar (AB, PA) or trypticase soy agar with 5% sheep's blood (SA, MRSA) plates at 37° C. Bacterial suspensions were prepared by placing bacteria into 10 mL trypticase soy broth (TSB) (BD Bioscience) with sterile cotton tip applicators, diluting 1:10 in TSB, measuring absorbance at 550 nM, and diluting with TSB using standard curves prepared for each bacterial strain to achieve 500 cfu/mL concentration. Sphingolipid-coated, uncoated, or vehicle-coated endotracheal tube segments were immersed in 2 mL bacterial suspension placed in 24 well plates and incubated for 12H at 37° C. Endotracheal tube segments were rinsed in 100 mL HEPES/saline (H/S) (132 mM NaCl, 20 mM HEPES [pH 7.4], 5 mM KCl, 1 mM $CaCl_2$, 0.7 mM $MgCl_2$, 0.8 mM $MgSO_4$) at 37° C., agitated at 125 RPM for 30 min. Segments were then placed in 10 mL sterile H/S in test tubes and sonicated at 37° C. in a bath sonicator for 10 min to remove adherent bacteria. Test tubes were vortexed for 5 seconds and the H/S serially diluted, plated on Lennox broth (LB) plates and incubated overnight. Bacterial colony forming units (cfu) were counted and the total amount of bacteria adherent to the 1 cm endotracheal tube segments was calculated. Results are set forth in FIG. 13.

Example 9

This Example illustrates durability of embodiments of the sphingosine coatings produced by methods described herein.

Plastic coverslips were tested for inhibition of bacterial adherence using a modified version of the international standard for measurement of antibacterial activity on plastics and other non-porous surfaces, ISO 22196. Bacteria were prepared as described above to a concentration of $1\times10^6$ cfu/mL. Ten µL (10,000 cfu) of bacterial suspension was then placed on the sphingolipid-coated and ethanol-coated portion of the coverslips and covered with a 2 cm×3 cm low density polyethylene (LDPE) plastic film and incubated for 24 hours at 37° C. The plastic film was removed and the plastic coverslips rinsed to remove planktonic bacteria. The coverslips were then placed into a drying rack and exposed to humidified air by incubating at 37° C. for 12 hours. Coverslips were placed into 10 mL sterile H/S in test tubes and sonicated at 37° C. in a bath sonicator for 10 min to remove adherent bacteria. Test tubes were vortexed for 5 seconds and the H/S serially diluted, plated on Lennox broth (LB) plates and incubated overnight. Bacterial colony forming units were counted and the total amount of bacteria adherent to the coverslips was calculated. Results are set forth in FIG. 14A.

To study the durability of the coating against bacterial adherence, the coated portion of the coverslip was inoculated with additional bacteria after 24 and 48 hours. Bacteria were prepared the same as initial inoculation ($1\times10^6$ cfu/mL). The LDPE plastic film was lifted, 10 µL (10,000 cfu) was pipetted onto the coated surface, and the LDPE film was replaced. The coverslips were incubated again for 24H and the inoculation was again repeated at 48 hours. At 72 hours, the coverslips were H/S rinsed to remove planktonic bacteria, placed in drying racks and incubated for 12 hours, sonicated in sterile H/S for 10 min, diluted, plated and quantification of adherent bacteria was performed. Results are set forth in FIG. 14B.

In order to visualize the adherent bacteria after 24 hours, a group of coverslips were stained as follows prior to the removal of adherent bacteria by sonication. Coverslips were removed from the incubator after being rinsed and dried in the humidifier for 12 hours. The adherent bacteria were heat-fixed to the coverslips by quickly passing over a Bunsen burner. The coverslips were then immersed in crystal violet for 1 min, serially rinsed in $H_2O$, and mounted with VectaMount permanent mounting media. Slides were imaged using standard light microscopy. Results are set forth in FIG. 15.

Example 10

This Example illustrates in vitro biofilm colonization upon including incubation in humidified air after complete immersion in order to more closely approximate in vivo conditions relevant to the tube environment in an intubated patient.

Endotracheal tubes in vivo may be adjacent to respiratory epithelial cells and a thick mucous layer, but are also primary exposed to humidified air. To more closely replicate the in vivo conditions, a variation of our methods described above in Example 8 was developed. Endotracheal tube segments were coated as described in Example 7. Bacterial suspensions were prepared and endotracheal tube segments were placed into 24 well plates as described in Example 8. After 24 hours of incubation, however, the endotracheal tube segments were rinsed in 50 mL sterile H/S, suspended in air by sticking them with a 1 mL insulin needle, and incubating in humidified air at 37° C. for 24 hours. Adherent bacteria were released from the surface and quantified as described in Example 8.

Example 11

This example illustrates characterization of a specific embodiment of a Sphingolipid coated ETT prepared according to methods disclosed herein.

Endotracheal tube segments were dip coated with sphingolipid vs. vehicle as described in Example 7 to form a thin film coating. Samples were prepared as follows; coated segments were stained with 0.1% osmium tetroxide (Sigma) in $H_2O$ for 30 min then rinsed in $H_2O$ for 5 min. Segments were dried and transported to the SEM lab. Segments were cut to fit on standard aluminum specimen mounts and placed on the mounts using conductive tape. Mounted segments were then sputter coated with gold/platinum for 15 s and imaged using scanning electron microscopy (SEM) (FEI/Phillips XL-30 SEM) (as set forth in FIGS. 17A-17F, FIGS.

20A-20F and FIGS. 21A-21F). To study the durability of the coating in aqueous solutions samples were immersed in $H_2O$ (FIGS. 20C and 20D; and FIGS. 21A and 21B), H/S (FIGS. 20E and 20F, and FIGS. 21C and 21D), or PBS (FIGS. 21E and 21F) for either 12 H (FIGS. 20C-20F) or 7 days (FIGS. 21A-21F) at 37° C. Samples were then stained and imaged as described above.

Example 12

This Example describes quantification of Sphingolipid on ETTs utilizing mass spectrometry in accordance with specific embodiments herein.

Coated plastic surfaces were extracted by a one-step lipid extraction. Briefly, a plastic piece was transferred into a siliconized glass tube and adsorbed sphingosine was extracted by addition of 10 mL methanol and sonification on ice for 1 hour. After centrifugation, the lipid extract was diluted with methanol and 50 pmol of $C_{17}$-sphingosine was added as internal standard. Sphingosine species were separated by reverse-phase high performance liquid chromatography (HPLC) (Agilent 1260 series, Agilent Technologies, Waldbronn, Germany) using a Waters X-Bridge C18 separation column (4.6 mm×150 mm, 3.5 µm particle size, 138 Å pore size) with a Waters X-Bridge C18 guard column (4.6×20 mm; Waters, Eschborn, Germany). Solvent A was 50:50 methanol-acetonitrile with 0.1% formic acid and solvent B was water with 0.1% formic acid. The gradient was increased from 72% A to 100% A between 0 min and 6 min, held at 100% A between 6 and 12 min, returned to 72% A between 12 and 13 min and held at 72% A for 4 min to allow column reequilibration. The flow rate was 0.6 mL/min between 0 min and 5 min, increased from 0.6 mL/min to 1.0 mL/min between 5 min and 6 min, held at 1.0 mL/min between 6 min and 12 min, returned to 0.6 mL/min between 12 and 13 min. The HPLC column effluent was introduced onto an Agilent 6490 triple quadrupole-mass spectrometer (Agilent Technologies) operating in the positive ESI mode. The following ion source parameters were used: drying gas temperature 290° C., drying gas flow 11 L/min of nitrogen, sheath gas temperature 380° C., sheath gas flow 12 L/min nitrogen, nebulizer pressure 35 psi, capillary voltage 4500V. Ion funnel parameters were: high pressure RF voltage 110 V and low pressure RF voltage 60 V. Multiple reaction monitoring (MRM) transition 300.3 m/z>282.3 m z at 8 eV collision energy was used for quantification of sphingosine, whereas MRM transition 286.3 m/z>268.3 m/z at 8 eV collision energy was used for quantification of C17-sphingosine. Quantification was performed with Mass Hunter Software (Agilent Technologies).

Example 13

This Example describes quantification of Sphingolipid on ETTs utilizing a Sphingokinase assay in accordance with specific embodiments herein.

Plastic pieces were extracted in $CHCl_3/CH_3OH/1N$ HCl (100:100:1, v/v/v), the lower phase was dried and resuspended in a detergent solution (7.5% [w/v] n-octyl glucopyranoside, 5 mM cardiolipin in 1 mM diethylenetriaminepentaacetic acid (DTPA)). The kinase reaction was initiated by addition of 0.004 units sphingosine kinase in 50 mM HEPES (pH 7.4), 250 mM NaCl, 30 mM $MgCl_2$ 1 µM ATP and 5 µCi [$^{32}$P]γATP. Samples were incubated for 60 min at 37° C. with shaking (350 rpm), then extracted in 20 µl 1N HCl, 800 µl $CHCl_3/CH_3OH/1N$ HCl (100:200:1, v/v/v), 240 µl $CHCl_3$ and 2 M KCl. The lower phase was collected, dried, dissolved in 20 µL of $CHCl_3:CH_3OH$ (1:1, v/v) and separated on Silica G60 thin layer chromatography (TLC) plates using $CHCl_3/CH_3OH$/acetic acid/$H_2O$ (90:90:15:5, v/v/v/v) for SPH. The TLC plates were analyzed using a phosphoimager.

Example 14

This Example illustrates bacterial adherence to endotracheal tubes comprising various embodiments of sphingosine coatings.

Figure 13B:
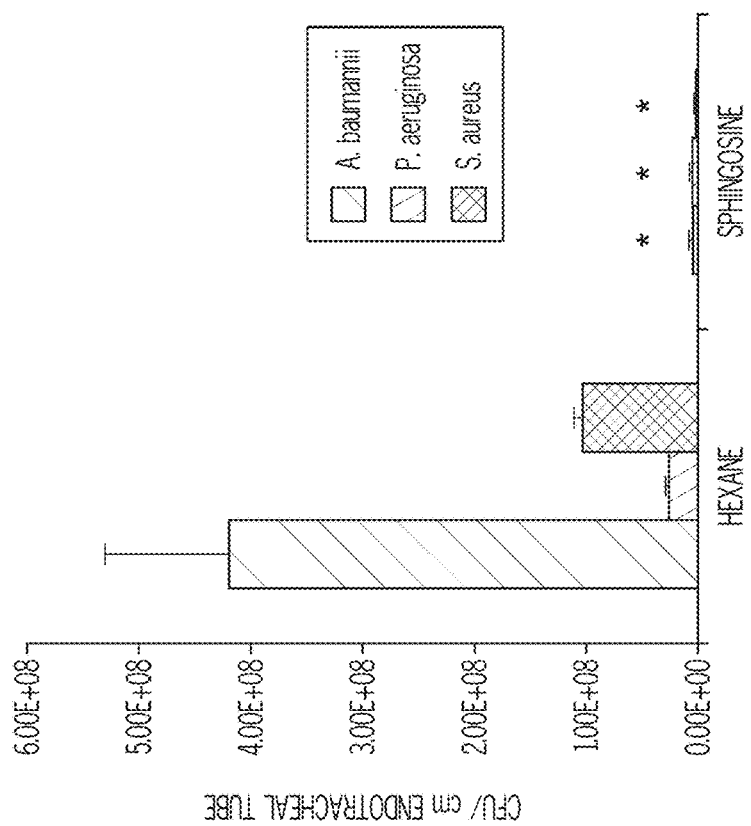
FIG. 13A) bar graph showing antimicrobial efficacy of sphingosine and phytosphingosine-coated 1 cm long segments of standard ET tubes after complete immersion in bacterial suspension; in vitro bacterial adherence of AB, PA and SA to uncoated vs vehicle (hexane)-coated vs sphingosine-coated; 13B) vehicle (acetone)-coated vs. phytosphingosine-coated.
Figure 13A:
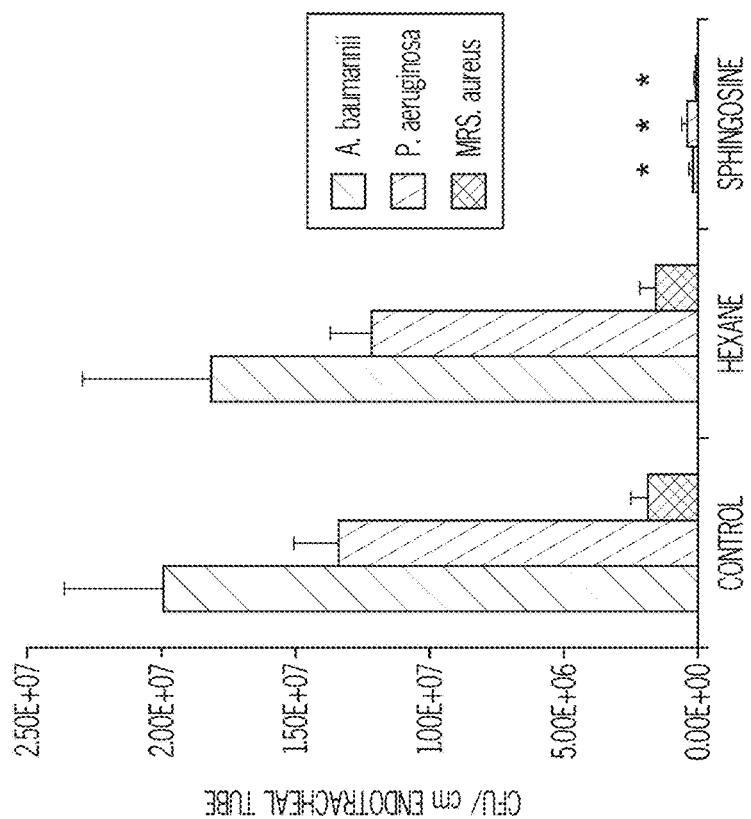
Figure 15A:
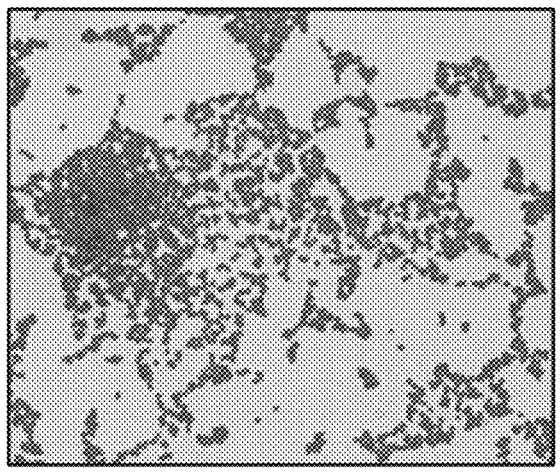
FIG. 15A) micrograph showing in vitro AB bacterial adherence to ethanol-coated plastic coverslip; 15B) AB bacterial adherence to phytosphingosine-coated coverslip; 15C) in vitro PA bacterial adherence to ethanol-coated plastic coverslip; 15D) PA bacterial adherence to phytosphingosine-coated coverslip; 15E) in vitro MRSA bacterial adherence to ethanol-coated plastic coverslip; and 15F) MRSA bacterial adherence to phytosphingosine-coated coverslip.
Figure 15B:
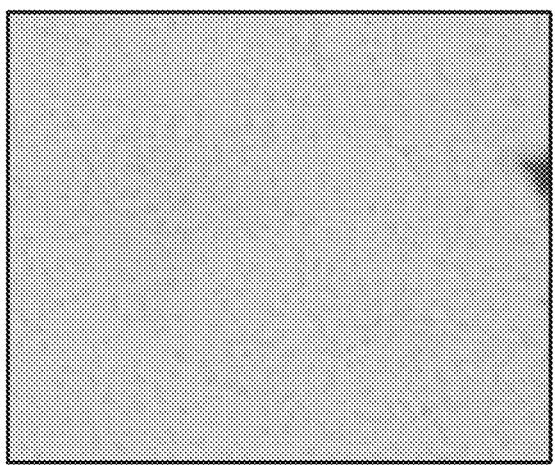
Figure 15C:
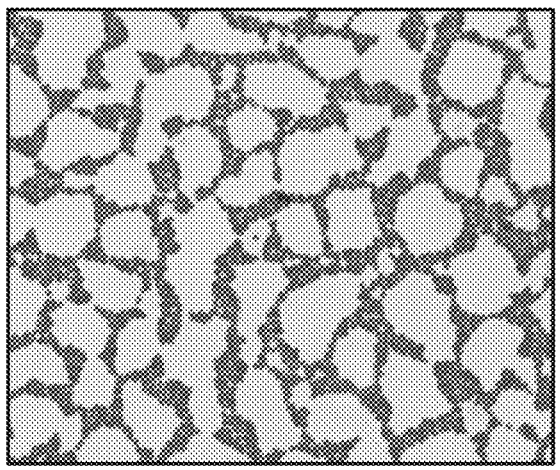
Figure 15D:
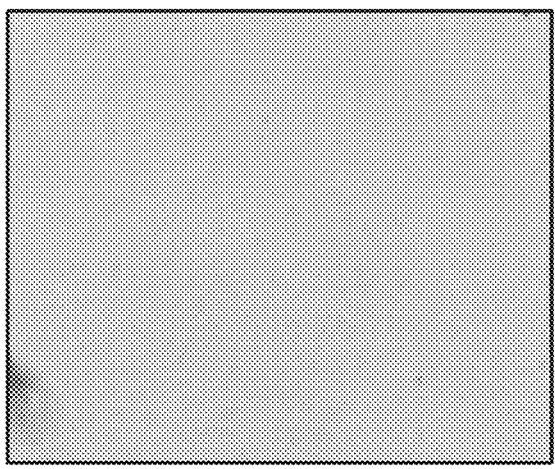
Figure 15E:
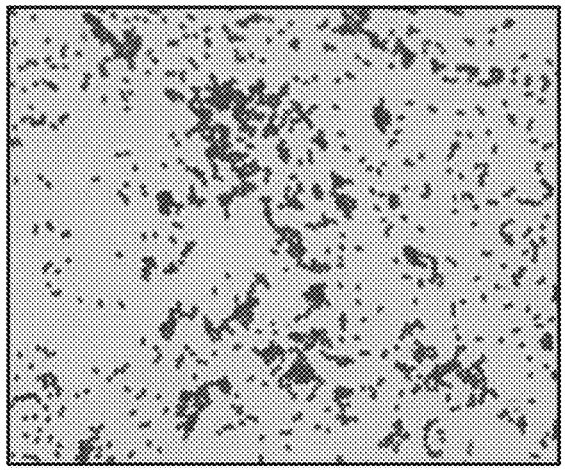
Figure 15F:
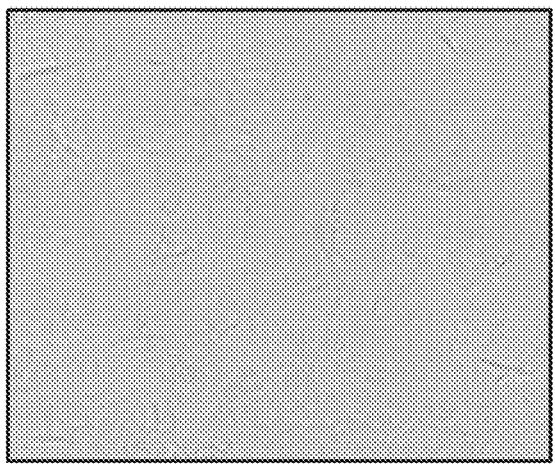

Endotracheal tubes were coated with sphingosine and phytosphingosine in reagent grade hexane and acetone, respectively. Coating tube segments with solvent did not significantly affect the adherence of AB, PA, or MRSA to the surface of the PVC compared to uncoated controls (p=0.78, 0.63, 0.73, respectively). FIGS. 13A and 13B, show in vitro bacterial adherence of AB, PA, and SA to (FIG. 13A) uncoated vs vehicle (hexane)-coated vs sphingosine-coated and (FIG. 13B) vehicle (acetone)-coated vs phytosphingosine-coated 1 cm long segments of standard PVC endotracheal tubes. Each tube segment was placed into bacterial suspension containing 1k cfu in growth media and incubated for 12H at 37° C. Tube segments were then rinsed in H/S and sonicated to release adherent bacteria. The Sphingosine-coated and Phytosphingosine-coated tube segments provided significant reductions in AB, PA, and MRSA adherence. Isolation of bacteria adherent to sphingosine-coated tube segments revealed $1.15 \times 10^5$ cfu/1 cm segment, $4.05 \times 10^5$ cfu/1 cm segment, and $6.67 \times 10^4$ cfu/1 cm segment compared to hexane-coated segments, $1.82 \times 10^7$ cfu/1 cm segment, $1.22 \times 10^7$ cfu/1 cm segment, and $1.57 \times 10^6$ cfu/1 cm segment of AB, PA, and MRSA, respectively. Isolation of bacteria adherent to phytosphingosine-coated segments revealed $4.18 \times 10^6$ cfu/1 cm segment, $2.58 \times 10^6$ cfu/1 cm segment, and $6.38 \times 10^5$ cfu/1 cm segment compared to acetone-coated segments, $4.22 \times 10^8$ cfu/1 cm segment, $2.50 \times 10^7$ cfu/1 cm segment, and $1.03 \times 10^8$ cfu/1 cm segment, respectively.

FIG. 13A shows that hexane-coated segments did not significantly reduce the number of adherent bacteria. Sphingosine-coated segments prevented 99.4% (p<0.005), 97% (p<0.005), and 97% (p=0.05) bacterial adherence of AB (n=6), PA (n=6), and SA (n=3), respectively. FIG. 13B shows that Phytosphingosine-coated segments prevented 99.0% (p=0.009), 90% (p<0.005), and 99.4% (p<0.005) bacterial adherence of AB (n=5), PA (n=5), and SA (n=5), respectively.

Example 15

This Example illustrates an embodiment of coating optimization.

Quantifying bacteria adherent to surfaces after 24 hour incubation immersed in bacterial suspension reaching greater than $10^7$ cfu/mL (data not shown) is not the most clinically relevant model of biofilm formation on endotracheal tubes. Endotracheal tubes in vivo are inoculated with bacteria which adhere to the surface prior to biofilm formation. The source of the bacterial inoculant (i.e. oral secretions, gastric reflux, inhaled droplets, etc.) has been reviewed multiple times (e.g. De Souza et al. 2014). Regardless of the mechanism, bacteria adherent to the surface of an endotracheal tube are likely subjected to an environment exposed to humidified air. Thus, to simulate this condition, the antimicrobial assay was modified. Further, bacteria adherent to endotracheal tubes were difficult to image via microscopy secondary to the curved nature of the tube. Thus, flat plastic coverslips were coated as a surrogate for PVC endotracheal tubes.

The antimicrobial assay utilized is a variation of the international standard, ISO 22196 Test for Antimicrobial Activity of Plastics. Briefly, 10,000 cfu of AB, PA, or MRSA in 10 µL TSB bacterial growth media was placed on the coated coverslips, covered with a 2 cm×3 cm piece of low density polyethylene plastic film, incubated at 37° C. for 24 hours and rinsed. In order to simulate the environment of an endotracheal tube in vivo, the coverslips were then suspended in air and incubated at 37° C., 100% humidity for 12 hours.

FIG. 14A and FIG. 14B summarize the data showing antimicrobial efficacy of phytosphingosine coated plastic. For FIG. 14A, bacterial suspensions containing 10,000 cfu in growth media were pipetted onto plastic coverslips, covered with plastic film and incubated for 24 hours at 37° C. Coverslips were rinsed with H/S, incubated for 12 hours, adherent bacteria were released from the surface via sonication, and plated. Phytosphingosine-coated coverslips prevented 96% ($p=0.02$), 99% ($p=0.006$), and 93% ($p<0.005$) bacterial adherence of AB (n=20), PA (n=15), and MRSA (n=20), respectively. For FIG. 14B bacterial suspensions containing 10,000 cfu in growth media were pipetted onto plastic coverslips, covered with plastic film and incubated for 24 hours. Additional suspensions of 10,000 cfu were pipetted onto the coverslips after 24 hours and 48 hours. At 72 hours, coverslips were rinsed in H/S, incubated for 12 hours, and adherent bacteria were released via sanitation, and plated. Phytosphingosine-coated coverslips prevented 93% ($p=0.005$), 94% ($p=0.005$), and 99% ($p=0.03$) bacterial adherence of AB (n=3), PA (n=3), and MRSA (n=3), respectively.

FIGS. 15A-15F are a series of micrographs demonstrating the antimicrobial efficacy of phytosphingosine-coated plastic. The in vitro bacterial adherence of AB, PA, and MRSA to vehicle (ethanol)-coated (FIGS. 15A, 15C, and 15E) coverslips was compared to phytosphingosine-coated (FIGS. 15B, 15D, and 15F) plastic coverslips. Adherent bacteria were not isolated via sonication; rather they were heat fixed to the plastic slide, stained with crystal violet, and mounted on glass slides as described in Example 9.

The coverslips were coated with phytosphingosine as previously described resulting in a 2.4 cm×4 cm area of coated plastic which was then subjected to the variation of ISO 22196. As shown in FIG. 14A, phytosphingosine-coated plastic significantly reduced AB, PA, and MRSA adherence. Isolation of AB, PA, and MRSA adherent to phytosphingosine-coated plastic revealed bacterial counts of $1.74\times10^5$ cfu, $3.43\times10^4$ cfu, and $2.75\times10^5$ cfu compared to ethanol-coated, $4.68\times10^6$ cfu, $4.59\times10^6$ cfu, and $4.01\times10^6$ cfu, respectively.

In order to assess the durability of the phytosphingosine coating against bacteria, the above protocol was performed with the addition of a second and third inoculation of 10,000 cfu of AB, PA, or MRSA in 10 µL TSB bacterial growth media at 24 hour and 48 hour time points. After 72 hours, rinsing, dry incubation, and sonication were performed. As shown in FIG. 14B, the anti-adherent properties of phytosphingosine-coated plastic were found to be durable at least up to 72 hours. Isolation of adherent AB, PA, and MRSA to phytosphingosine-coated plastic revealed counts of $1.45\times10^5$ cfu, $4.33\times10^5$ cfu, and $2.62\times10^4$ cfu compared to ethanol-coated, $2.17\times10^6$ cfu, $7.33\times10^6$ cfu, $9.37\times10^6$ cfu, respectively.

Example 16

This example illustrates determination of bacterial adherence to an embodiment of an optimized ETT coating.

After optimizing an embodiment of the coating process utilizing plastic coverslips as a surrogate for PVC endotracheal tube segments, the antimicrobial assay was repeated with the following modification; instead of utilizing a small volume of bacterial suspension and covering with a plastic film, the endotracheal tube segments were incubated by complete immersion followed by rinsing and suspension in air at 37° C., 100% humidity for 24 hours.

Figure 16:
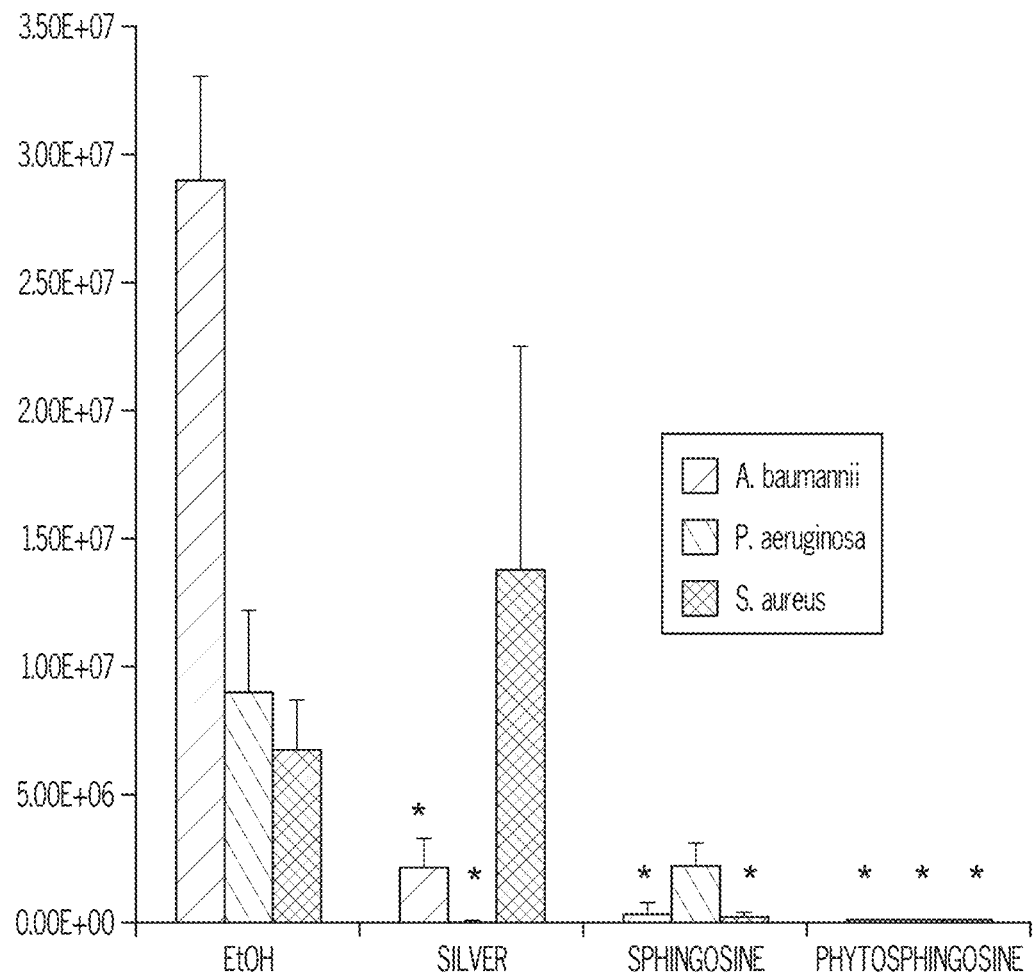
FIG. 16) bar graph comparing in vitro bacterial adherence of AB, PA, SA to vehicle (ethanol)-coated, silver-coated, sphingosine-coated, and phytosphingosine-coated 1 cm long segments of 8.0 standard polyvinyl chloride endotracheal tubes.
Figure 17A:
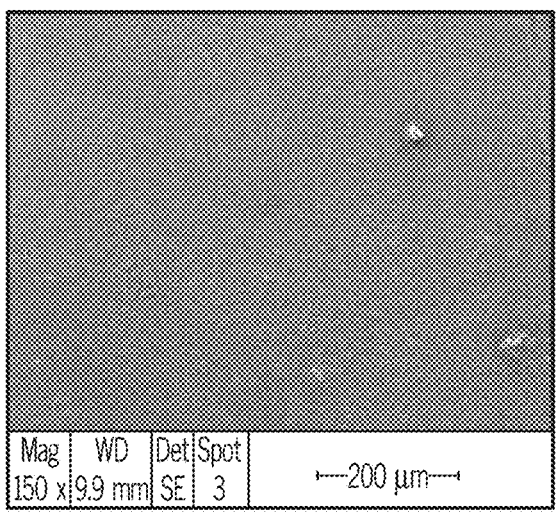
FIG. 17A) micrograph 150× image of ET tube surface single dip-coated in 30 mM sphingosine in 100% ethanol, 17B) micrograph 100× image of ET tube surface single dip-coated in 30 mM phytosphingosine in 100% ethanol, 17C) micrograph 5000× image of ET tube surface single dip-coated in 30 mM sphingosine in 100% ethanol, 17D) micrograph 1000× image of ET tube surface single dip-coated in 30 mM phytosphingosine in 100% ethanol, 17E) micrograph 25000× image of ET tube surface single dip-coated in 30 mM sphingosine in 100% ethanol, 17F) micrograph 25000× image of ET tube surface single dip-coated in 30 mM phytosphingosine in 100% ethanol.
Figure 17B:
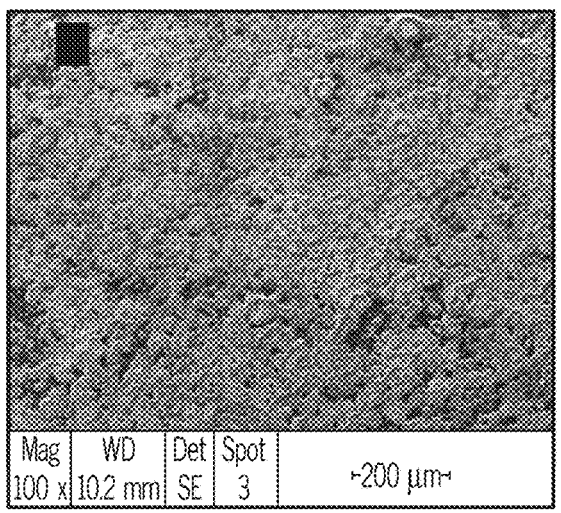
Figure 17C:
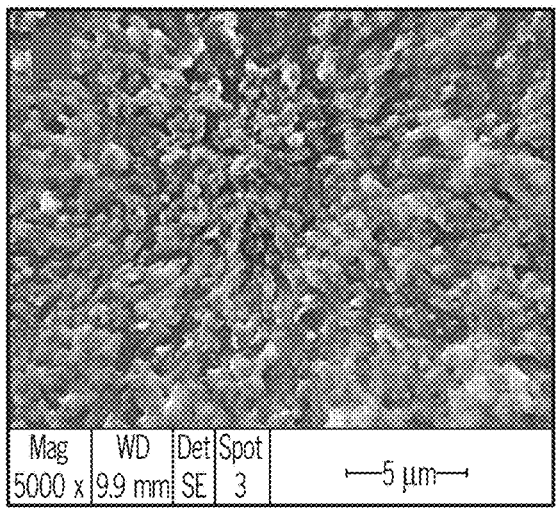
Figure 17D:
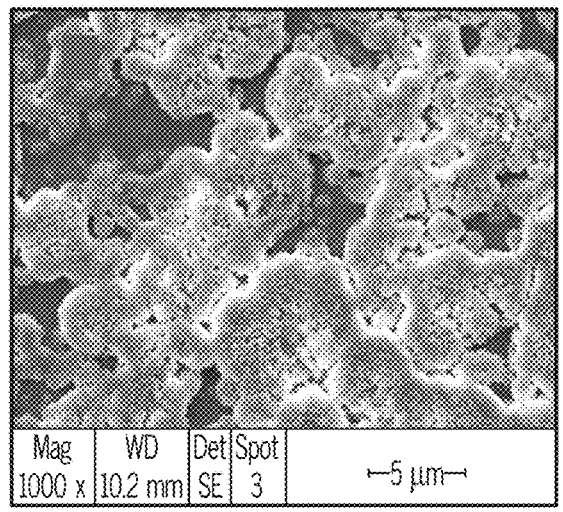
Figure 17E:
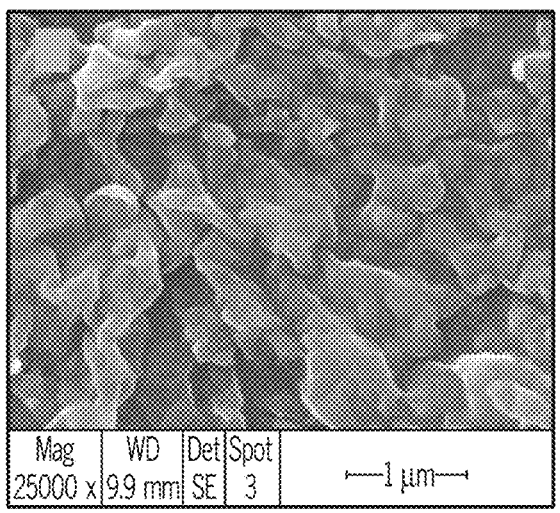
Figure 17F:
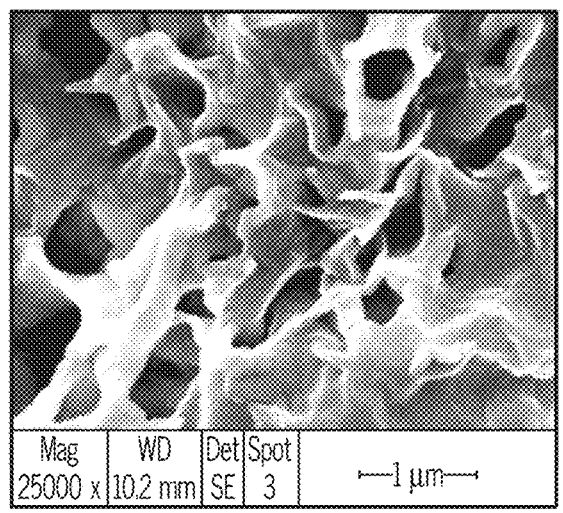

FIG. 16 summarizes data demonstrating and comparing the antimicrobial efficacy of silver-coated (Bard), sphingosine-coated, and phytosphingosine-coated endotracheal tubes after immersion and subsequent air incubation at 37° C., 100% humidity. In vitro bacterial adherence of AB, PA, and SA to vehicle (ethanol)-coated, commercially available silver-coated, sphingosine-coated, and phytosphingosine-coated 1 cm long segments of 8.0 standard polyvinyl chloride endotracheal tubes. Each tube segment was incubated in bacterial suspension containing 1k cfu in TSB growth media, incubated at 37° C. for 24 hours, rinsed in 50 mL H/S, incubated suspended in air at 37° C. for 24 hours, sonicated for 15 min to release adherent bacteria, and plated. Silver-coated segments prevented 93% ($p<0.005$) and 99.99% ($p=0.05$) bacterial adherence of AB, and PA, but did not prevent adherence of SA compared to vehicle-coated controls. Sphingosine-coated segments prevented 99% ($p<0.005$), 75% (not statistically significant, $p=0.13$), and 97% ($p=0.008$) and phytosphingosine-coated segments prevented 99.98% ($p<0.005$), 99.6% ($p=0.05$), and 99.94% ($p=0.006$) bacterial adherence of AB (n=4), PA (n=4), and SA (n=8), respectively.

As shown in FIGS. 17A-17F, sphingosine-coated and phytosphingosine-coated endotracheal tube segments provided significant reduction in AB and SA adherence, and phytosphingosine-coated endotracheal tube segments provided significant reduction in PA adherence. Isolation of AB, PA, and SA to sphingosine-coated and phytosphingosine-coated segments revealed counts of $3.87\times10^5$, $2.23\times10^6$, $2.28\times10^5$ cfu and $5.40\times10^3$, $3.48\times10^4$, $4.06\times10^3$ cfu, respectively, compared to ethanol-coated segments which had counts of $2.90\times10^7$, $9.03\times10^6$, and $6.72\times10^6$ cfu, respectively. There were no statistically significant differences between sphingosine-coated and phytosphingosine-coated segments compared to silver, which revealed AB, PA, and SA counts of $2.14\times10^6$, $1.00\times10^3$, and $1.38\times10^7$ cfu, respectively. However phytosphingosine-coated segments showed a trend toward less AB (99.8%, $p=0.15$) and SA (99.97%, $p=0.16$) adherence compared to silver and silver showed a trend toward less PA (97.1%, $p=0.05$) compared to phytosphingosine.

Example 17

This example illustrates characterization of specific embodiments of sphingolipid-coated endotracheal tubes.

Sphingosine and phytosphingosine are molecules found on various biological membranes of living organisms. They are also classified as nonionic biosurfactants. Adsorption of surfactants onto solid surfaces in aqueous solutions is a well studied process. Multiple mathematical models have been developed to characterize this process (i.e. Langmuir isotherms). These models describe a process by which a monolayer (or bilayer) of surfactant molecules adsorb onto solid surfaces. Any attempt at increasing the aqueous concentration of the surfactant in order to increase the adsorption is limited by the critical micelle concentration of the surfactant. Therefore, adsorption of a coating thicker than a mono- or bilayer is a laborious processes (i.e. Langmuir-Blogett films). Our method of evaporative-induced deposition of nonionic surfactants is not limited by the same parameters. As shown in FIGS. 17A-17F, specific embodiments of the coating method result in adsorption of 3-dimensional surfactant structures with features as large as 20 µm in diameter. These 3 dimensional structures contain large amounts of adsorbed surfactant compared to monolayers (or bilayers) while still being less than 10 µm in thickness. In order to prepare the micrographs of FIGS. 17A-17F, Sphingosine and phytosphingosine coated endotracheal tubes were prepared. 1 cm segments of endotracheal tubes were dip-coated once in 30 mM sphingosine (FIGS. 17A, 17C, and 17E) or 30 mM phytosphingosine (FIGS. 17B, 17D, and 17F) in 100% ethanol heated to 70° C. Segments were then stained with 0.1% osmium tetroxide, sputter-coated with gold/platinum, and imaged with scanning electron microscopy. Images obtained at several different magnifications.

Example 18

This example illustrates quantification of sphingosine in a coating by two different methods.

Figure 18A:
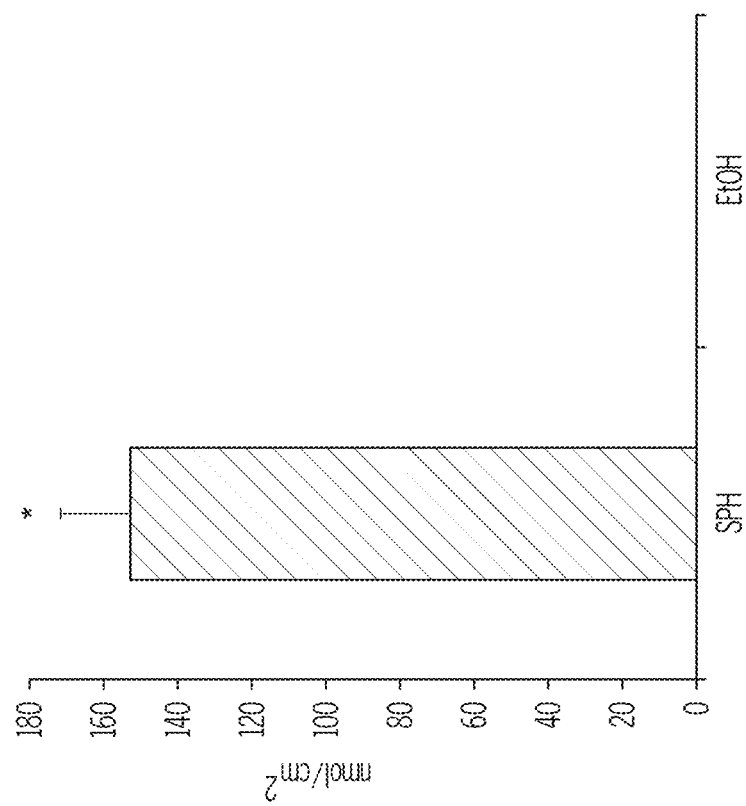
FIG. 18A) quantification of sphingosine on plastic slip extracted and analyzed by mass spectrometry, 18B) quantification of sphingosine on plastic slip extracted and analyzed by sphingosine kinase assay.
Figure 18B:
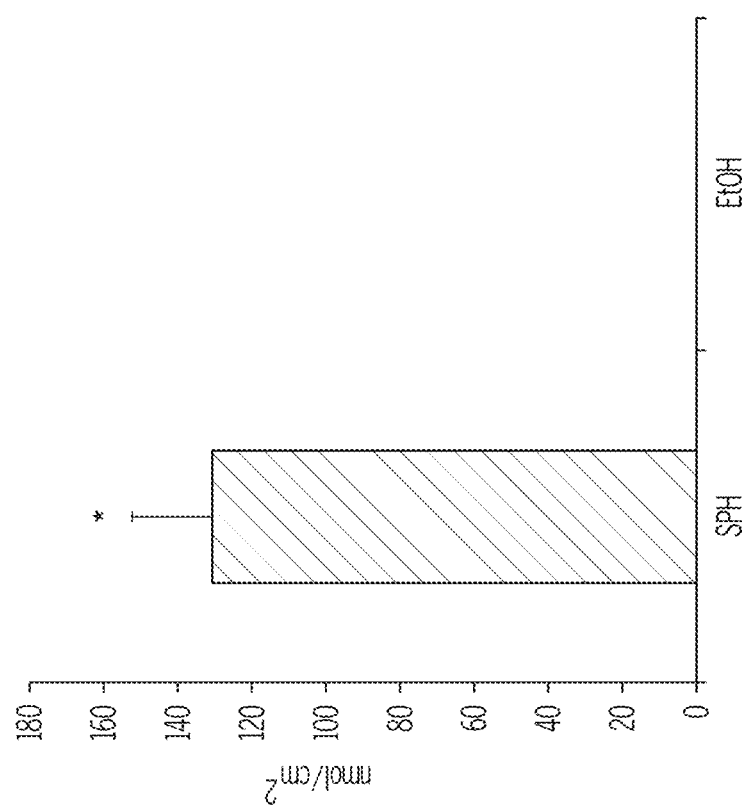

To determine the total amount of sphingosine present on the surface of the endotracheal tubes after dip coating, we performed mass spectrometry (FIG. 18A) and a sphingosine kinase radioactivity assay (FIG. 18B). Both methods confirmed a concentration of sphingosine in the nmol to µmol range per $cm^2$. This is an impressive amount as sphingosine has been shown to kill bacteria in solution with concentrations of nmol/L to µmol/L. Endotracheal tube segments were prepared by dip coating in a heated organic sphingosine solution as described above. Sphingosine was either extracted and analyzed by mass spectrometry (FIG. 18A) or sphingosine kinase assay (FIG. 18B). The amount of sphingosine calculated on the surface after dip coating is (A) 131 $nmol/cm^2$ and (B) 152.5 $nmol/cm^2$, respectively.

Example 19

This Example shows determination of durability of specific embodiments of sphingolipid coatings.

Figure 19:
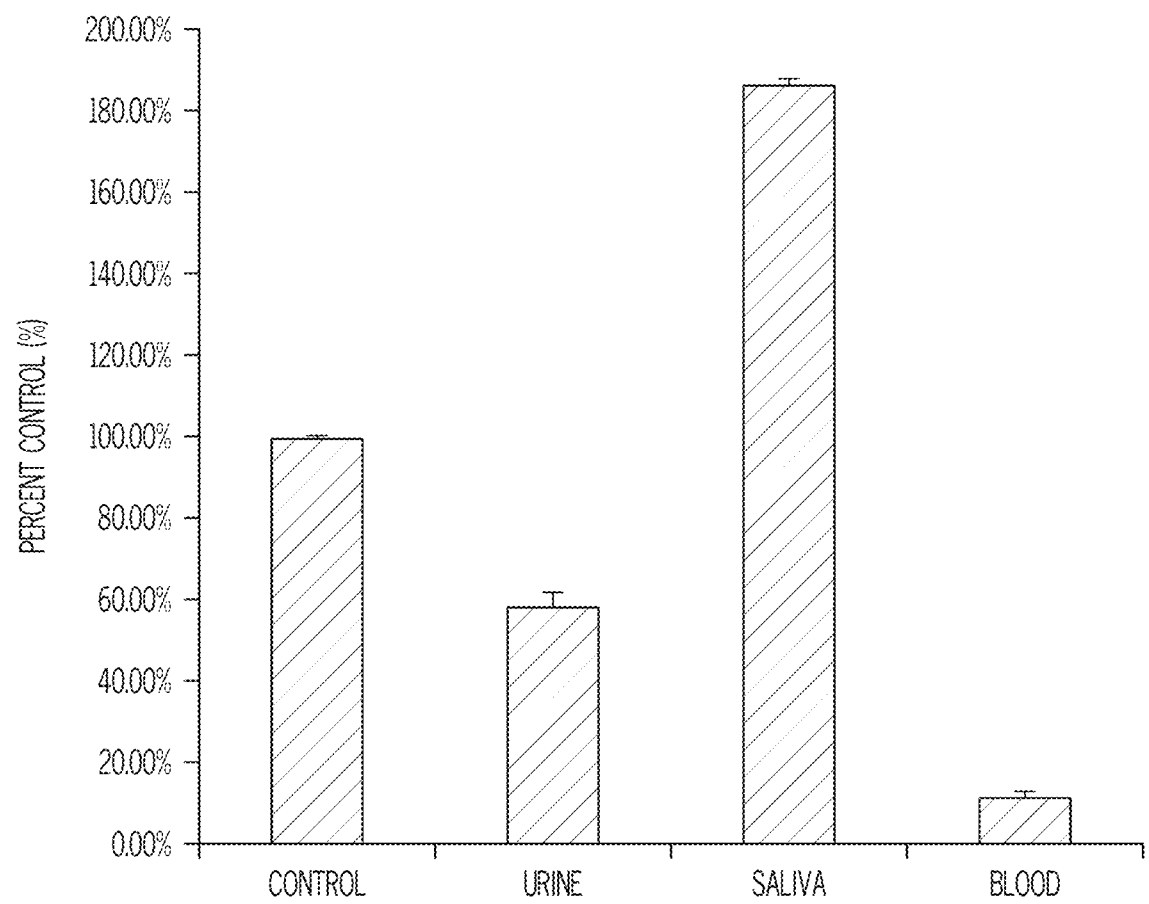
FIG. 19) bar graph comparing durability of a sphingosine coated endotracheal tube upon immersion in urine, saliva, blood or control and incubated at 37° for 7 days.

Any antimicrobial coating applied to endotracheal tubes (or any medical device) must have stability and durability when immersed in biological fluids. Thus, the durability of sphingosine coating in urine, blood, saliva for 7 days was quantified by sphingosine kinase assay and in water, H/S, and PBS imaged with electron microscopy. As shown in FIG. 19, the sphingosine coating was most stable in saliva followed by urine and then blood. The amount of sphingosine quantified after soaking in saliva was nearly double (186%) of control. This indicates that sphingosine present in the saliva was adherent to the previously sphingosine-coated endotracheal tube pieces. Some nonionic surfactants are very soluble in water, and a high amount of adsorbed surfactant becomes solubilized when placed back in aqueous solution. However, sphingosine and phytosphingosine are nearly completely insoluble in water which confers a high degree of stability of sphingosine and phytosphingosine-coating when placed into aqueous solutions.

Figure 20A:
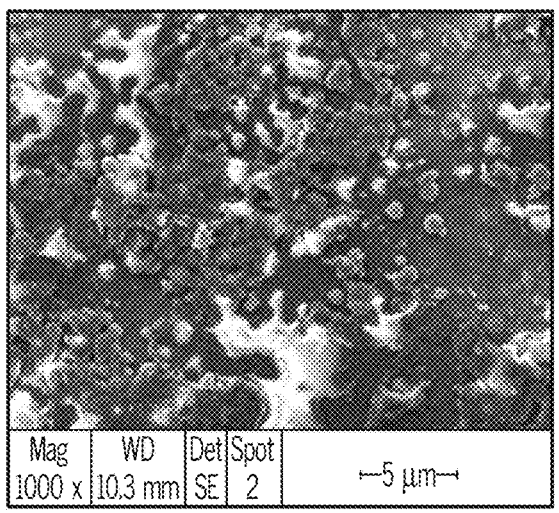
FIG. 20A) micrograph showing 3-D structure of phytosphingosine coating on a standard ET tube segment, 20B) micrograph showing 3-D structure of sphingosine coating on a standard ET tube segment, 20C) micrograph showing 3-D structure of phytosphingosine coating on a standard ET tube segment after immersion in water for 12 hours, 20D) micrograph showing 3-D structure of sphingosine coating on a standard ET tube segment after immersion in water for 12 hours, 20E) micrograph showing 3-D structure of phytosphingosine coating on a standard ET tube segment after immersion in H/S for 12 hours, 20F) micrograph showing 3-D structure of sphingosine coating on a standard ET tube segment after immersion in H/S for 12 hours.
Figure 20B:
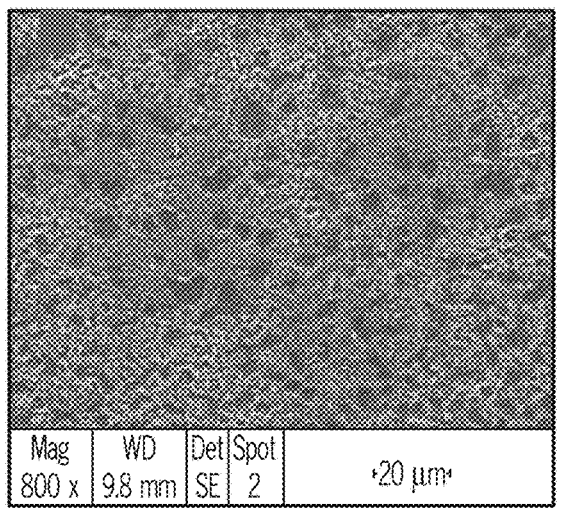
Figure 20C:
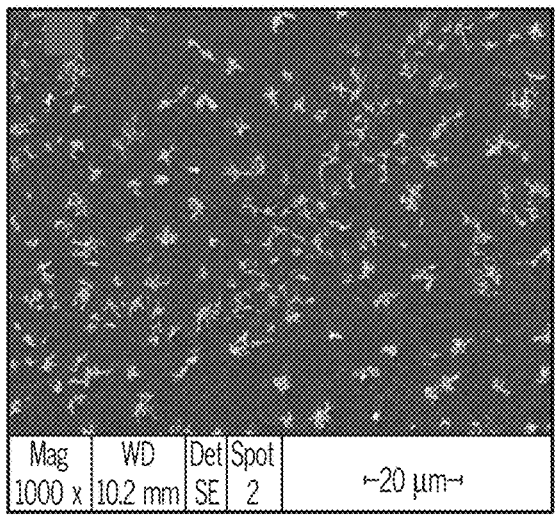
Figure 20D:
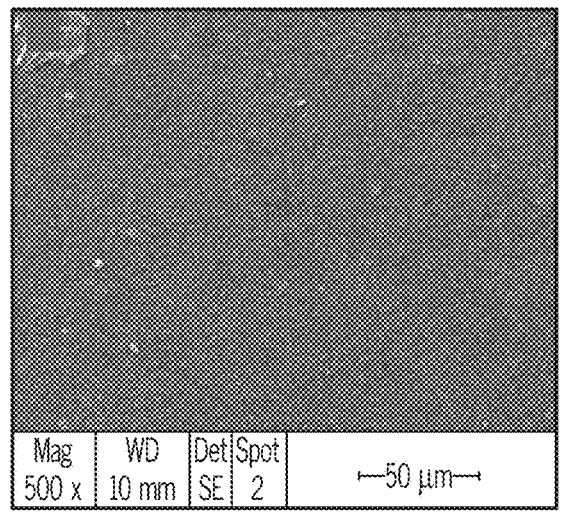
Figure 20E:
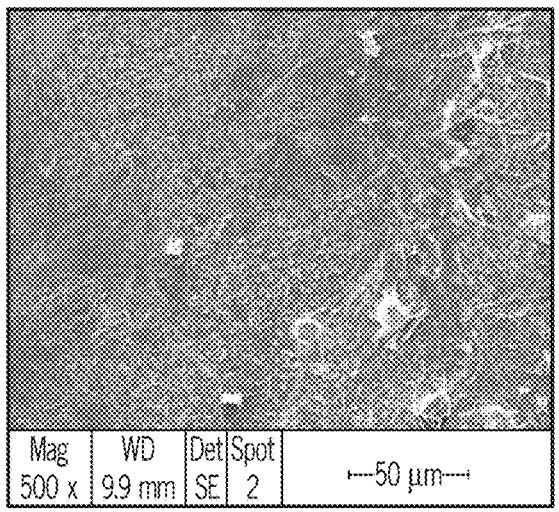
Figure 20F:
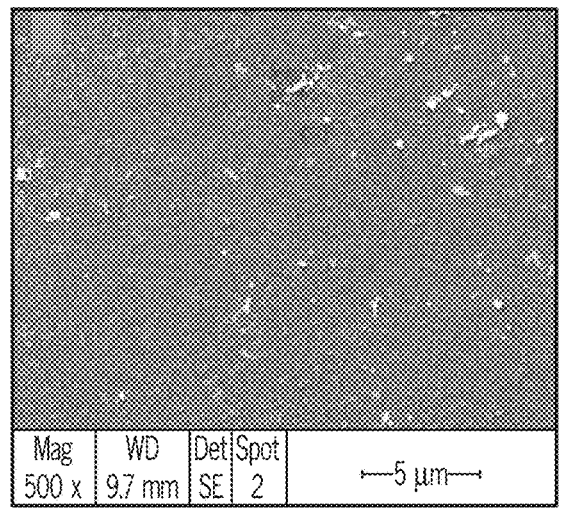

The micrographs of FIGS. 20A-20F and 21A-21F and show that the 3 dimensional structures of the sphingolipid coatings are stable in aqueous solutions after 12 hours (FIGS. 20C-20F) and 7 days (FIGS. 21A-21F). Sphingosine was quantified at the surface using the sphingosine kinase assay described in Example 13. Compared to control, 58% (n=3), 186% (n=3), and 11% (n=3) sphingosine remained on the surface of the endotracheal tube segments when placed in urine, saliva, and blood respectively. FIGS. 20C-20F shows Phytosphingosine and sphingosine coated PVC endotracheal tubes after 12 hours aqueous immersion. 1 cm segments of endotracheal tubes were dip-coated once in 75 mM phytosphingosine (FIG. 20A, FIG. 20C, FIG. 20E) or 90 mM sphingosine (FIG. 20B, FIG. 20D, FIG. 21F) in 100% ethanol heated to 70° C. Segments were unsoaked (FIG. 20A, FIG. 20B), soaked for 12 hours in H2O (FIG. 20C, FIG. 20D), or soaked for 12 hours in H/S (FIG. 20E, FIG. 20F). Segments were then stained with 0.1% osmium tetroxide, sputter coated with gold/platinum, and imaged with scanning electron microscopy.

Figure 21A:
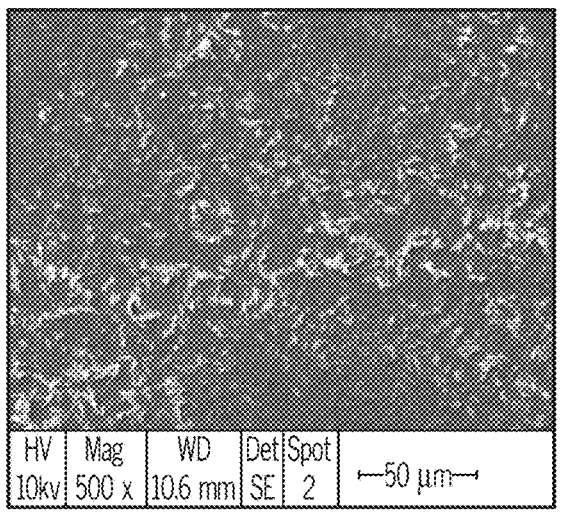
FIG. 21A) micrograph showing 3-D structure of phytosphingosine coating on a standard ET tube segment after immersion in water for 7 days, 21B) micrograph showing 3-D structure of sphingosine coating on a standard ET tube segment after immersion in water for 7 days, 21C) micrograph showing 3-D structure of phytosphingosine coating on a standard ET tube segment after immersion in H/S for 7 days, 21D) micrograph showing 3-D structure of sphingosine coating on a standard ET tube segment after immersion in H/S for 7 days, 21E) micrograph showing 3-D structure of phytosphingosine coating on a standard ET tube segment after immersion in PBS for 7 days, 21F) micrograph showing 3-D structure of sphingosine coating on a standard ET tube segment after immersion in PBS for 7 days.
Figure 21B:
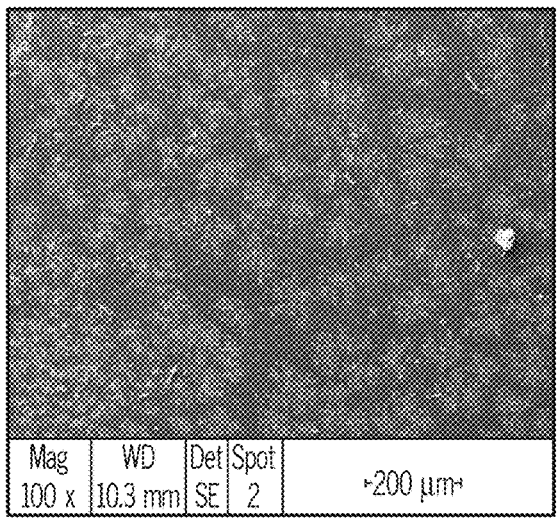
Figure 21C:
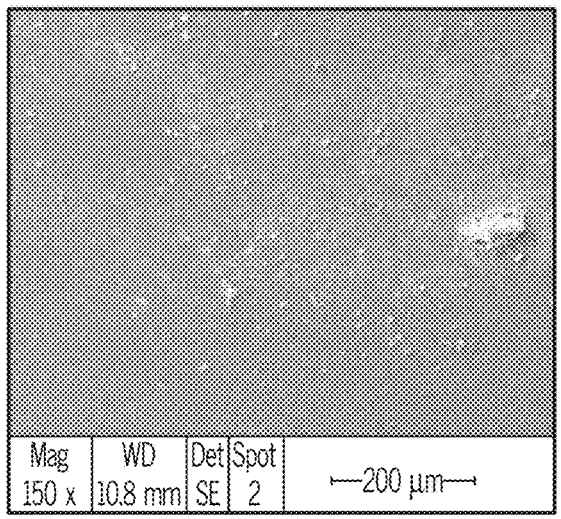
Figure 21D:
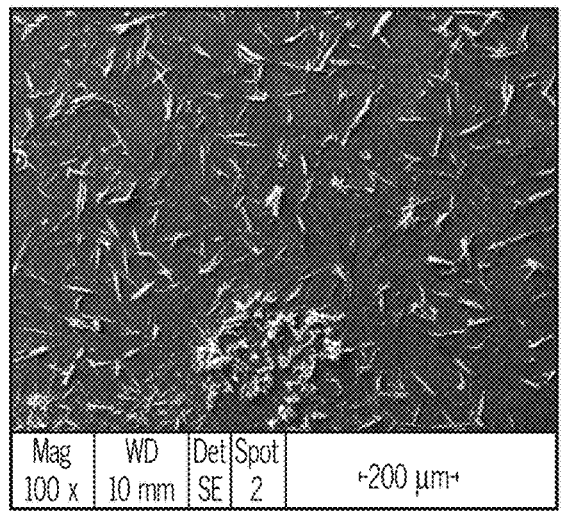
Figure 21E:
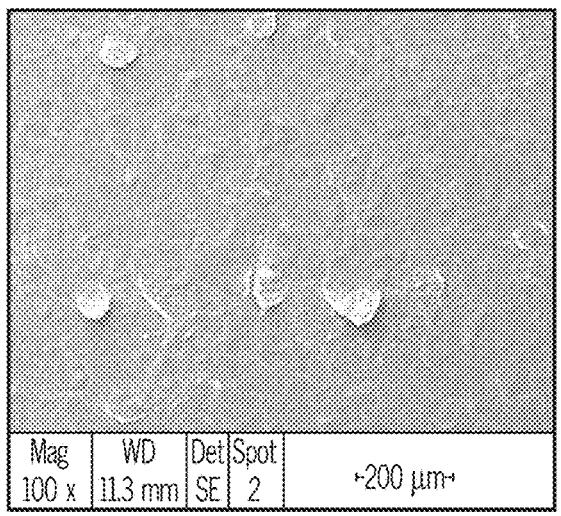
Figure 21F:
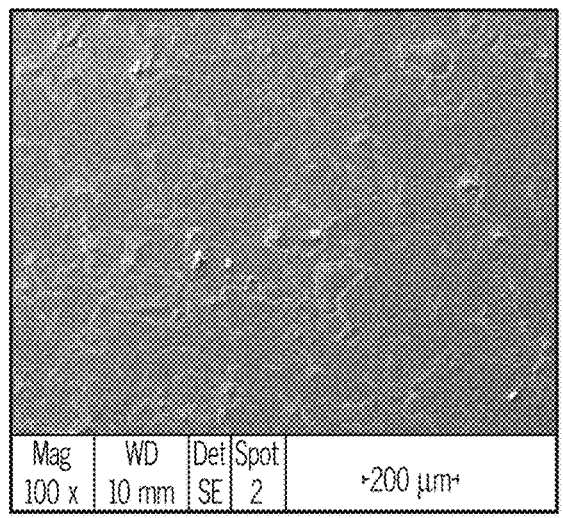

FIG. 21A-FIG. 21F show micrographs of Phytosphingosine and Sphingosine coated PVC endotracheal tubes after 7 days aqueous immersion. 1 cm segments of endotracheal tubes were dip-coated once in 75 mM phytosphingosine (FIG. 21A, FIG. 21C, FIG. 21E) or 90 mM sphingosine (FIG. 21B, FIG. 21D, FIG. 21F) in 100% ethanol heated to 70° C. Segments were soaked for 7 days in H2O (FIG. 21A, FIG. 21B), H/S (FIG. 21C, FIG. 21D), or PBS (FIG. 21E, FIG. 21F). Segments were then stained with 0.1% osmium tetroxide, sputter-coated with gold/platinum, and imaged by scanning electron microscopy.

Although embodiments of the invention have been exemplified and described with specificity, a person of ordinary skill in the art will understand that additional aspects and embodiments are within the scope of the claims as defined by the appended claims.

The invention claimed is:

1. A method for applying a three dimensional thin film sphingolipid aggregate coating to a surface of a substrate, the method comprising:
    a) providing a suspension consisting of an amount of sphingolipid suspended in a preheated medium-to-fast-evaporating organic solvent, wherein the sphingolipid is selected from one or more of sphingosine, phytosphingosine, and psychosine;
    b) applying energy to the suspension sufficient to create a colloidal dispersion of sphingolipid in the solvent, wherein applying energy comprises heating the suspension to a temperature within 10° C. of a boiling point of the medium-to-fast-evaporating solvent and sonicating the suspension at between about 20 kHz to about 40 kHz, wherein the heat and energy are applied until aggregates are not visible and the dispersion becomes a solution;
    c) coating the surface of the substrate with at least one application of the solution, each application followed directly by a solvent evaporation period, wherein coating comprises immersing the surface in the solution for 1 s and withdrawal from the solution at a rate of at least 1 cm/second,
    wherein the method deposits the sphingolipid in aggregates on the substrate surface to provide a three dimensional thin film coating that resists bacterial adhesion and biofilm formation, and wherein the three dimensional thin film coating is less than 10 µm thick.

2. The method according to claim 1, wherein step c) further comprises bringing the coated substrate to ambient temperature such that the solvent evaporation period takes place at room temperature.

3. The method according to claim 1, wherein the organic solvent of step (a) is a fast-evaporating organic solvent and fast evaporating is defined as exhibiting a vaporization rate under ambient conditions of greater than 3 based on an n-butyl acetate standard=1.

4. The method according to claim 3, wherein the solvent is selected from hexane, acetone, cyclohexane, and methyl ethyl ketone.

5. The method according to claim 1, wherein the organic solvent of step (a) is a medium-evaporating organic solvent and medium evaporating is defined as exhibiting a vaporization rate under ambient conditions of between 0.8 and 3.0, inclusive, based on an n-butyl acetate standard=1.

6. The method according to claim 5, wherein the solvent is selected from ethanol and naphtha.

7. The method according to claim 5, wherein the solvent is 95% to 100% ethanol.

8. The method according to claim 1, wherein step c) comprises at least 2 applications of coating.

9. The method according to claim 1, wherein step c) comprises at least 5 applications of coating.

10. The method according to claim 1, wherein the solvent evaporation period is sufficient for substantially complete evaporation of solvent.

11. The method according to claim 10, wherein the substantially complete evaporation of solvent is at least partially effectuated by one or more of air drying, blow-drying, vacuum-drying or heat-assisted drying.

12. The method according to claim 1, wherein sonicating comprises bath or probe sonicating.

13. The method according to claim 1, comprising sonicating the suspension at about 40 kHz.

14. The method according to claim 1, wherein the substrate is selected from glass, plastic or metal.

15. The method according to claim 1, wherein the sphingolipid comprises sphingosine and the solvent comprises hexane.

16. The method according to claim 1, wherein the sphingolipid comprises phytosphingosine and the solvent comprises acetone.

17. The method according to claim 1, wherein the sphingolipid comprises sphingosine or phytosphingosine and the solvent comprises ethanol.

18. The method of claim 1, wherein the amount of sphingolipid in the suspension is 30 mM.

19. A method for preventing or inhibiting the formation of a biofilm on a substrate, the method comprising coating the substrate with a coating applied according to a method defined by claim 1.

* * * * *